(12) United States Patent
Fujii

(10) Patent No.: US 11,574,504 B2
(45) Date of Patent: Feb. 7, 2023

(54) INFORMATION PROCESSING APPARATUS, INFORMATION PROCESSING METHOD, AND PROGRAM

(71) Applicant: Sony Corporation, Tokyo (JP)

(72) Inventor: Hiroyoshi Fujii, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 17/253,750

(22) PCT Filed: Jul. 12, 2019

(86) PCT No.: PCT/JP2019/027625
§ 371 (c)(1),
(2) Date: Dec. 18, 2020

(87) PCT Pub. No.: WO2020/022096
PCT Pub. Date: Jan. 30, 2020

(65) Prior Publication Data
US 2021/0286981 A1 Sep. 16, 2021

(30) Foreign Application Priority Data

Jul. 26, 2018 (JP) .............................. JP2018-140184

(51) Int. Cl.
*G06T 9/00* (2006.01)
*G06V 40/20* (2022.01)
(Continued)

(52) U.S. Cl.
CPC .............. *G06V 40/20* (2022.01); *G06V 10/96* (2022.01); *H04N 5/23219* (2013.01); *H04N 5/23296* (2013.01)

(58) Field of Classification Search
CPC .......... G06K 9/00335; G06K 9/00993; G06K 9/00221; G06K 9/00369; G06K 9/00771;
(Continued)

(56) References Cited

U.S. PATENT DOCUMENTS

2005/0157908 A1 7/2005 Matsugu et al.
2013/0332958 A1* 12/2013 Yang ..................... G01S 3/7864
725/38
(Continued)

FOREIGN PATENT DOCUMENTS

EP  2 679 140 A1  1/2014
JP  2004280643 A  10/2004
(Continued)

OTHER PUBLICATIONS

International Search Report dated Oct. 9, 2019 in PCT/JP2019/027625 filed on Jul. 12, 2019.

*Primary Examiner* — Stephen P Coleman
(74) *Attorney, Agent, or Firm* — Oblon, McClelland, Maier & Neustadt, L.L.P.

(57) ABSTRACT

Disclosed is an information processing apparatus including processing circuitry that sets a behavior detection parameter corresponding to a behavior of a subject based on input information corresponding to characteristics of a subject in an image, and detects a behavior of the subject based on the set behavior detection parameter and a posture of the subject in the image. The present disclosure can be applied to, for example, a lecture capturing system.

21 Claims, 27 Drawing Sheets

(51) Int. Cl.
*H04N 5/232* (2006.01)
*G06V 10/96* (2022.01)

(58) Field of Classification Search
CPC . H04N 5/23219; H04N 5/23296; G16H 30/40
USPC ........................................................ 382/103
See application file for complete search history.

(56) References Cited

U.S. PATENT DOCUMENTS

| | | |
|---|---|---|
| 2014/0002624 A1 | 1/2014 | Nemoto et al. |
| 2014/0204206 A1* | 7/2014 | Itoi .................... H04N 7/188 348/143 |
| 2016/0092733 A1* | 3/2016 | Loce .................... G06K 9/6212 382/103 |
| 2016/0092734 A1 | 3/2016 | Loce et al. |
| 2016/0203726 A1* | 7/2016 | Hibbs ...................... G09B 7/02 434/308 |
| 2016/0371547 A1* | 12/2016 | Valentino, III .... G06K 9/00771 |
| 2018/0121712 A1* | 5/2018 | Garrett ............... H04N 5/23299 |
| 2018/0174320 A1* | 6/2018 | Hayashi ............. G06K 9/00342 |
| 2020/0005511 A1* | 1/2020 | Kavidayal ............... G06N 3/088 |

FOREIGN PATENT DOCUMENTS

| | | |
|---|---|---|
| JP | 2008276455 A | 11/2008 |
| JP | 2009-26146 A | 2/2009 |
| JP | 2012-95019 A | 5/2012 |
| JP | 2014033265 A | 2/2014 |
| JP | 2016027452 A | 2/2016 |
| JP | 2018093347 A | 6/2018 |
| WO | WO-2016143641 A1 | 9/2016 |

* cited by examiner

FIG. 14

| FACE INFORMATION | NAME | PARAMETER | PERSONAL CHARACTERISTIC QUANTITY | AGE/GENDER |
|---|---|---|---|---|
| U1 | ○○ICHIRO | p11, p12 | f11, f12 | 12/MALE |
| U2 | ○○JIRO | p21, p22 | f21, f22 | 11/MALE |
| U3 | ○○SABURO | p31, p32 | f31, f32 | 11/MALE |
| U5 | ○○HANAKO | p51, p52 | f51, f52 | 12/FEMALE |
| U6 | ○○ROKURO | p61, p62 | f61, f62 | 11/MALE |

INFORMATION PROCESSING APPARATUS, INFORMATION PROCESSING METHOD, AND PROGRAM

TECHNICAL FIELD

The present disclosure relates to an information processing apparatus, an information processing method, and a program, and particularly, to an information processing apparatus, an information processing method, and a program capable of improving accuracy of behavior detection.

CROSS REFERENCE TO RELATED APPLICATIONS

This application claims the benefit of Japanese Priority Patent Application JP 2018-140184 filed on Jul. 26, 2018, the entire contents of which are incorporated herein by reference.

BACKGROUND ART

There is a method of setting some parameters according to information associated with a subject in an image.

For example, PTL 1 discloses a technology of setting a search area in a next frame on the basis of the age estimation and person identification result of a person who is a target of tracking in an image.

In addition, PTL 2 discloses an imaging apparatus that detects the size and inclination of a face of a subject in an image and sets parameters related to zooming on the basis of the detection result.

Meanwhile, there is known a behavior detection technology for detecting a behavior of a subject in an image. The behavior detection is performed on the basis of the result of posture detection of the subject and parameters used for the behavior detection.

The parameters used for the behavior detection are represented by positions of the body part corresponding to the detected behavior and the like. By comparing the positions of the body part of the subject in the image with the parameters used for the behavior detection, the behavior of the subject can be detected.

CITATION LIST

Patent Literature

PTL 1: JP 2009-26146A
PTL 2: JP 2012-95019A

SUMMARY OF INVENTION

Technical Problem

By the way, in many cases, the parameters used for the behavior detection are set in advance by a system designer. However, since the physical characteristics such as height and physique vary from subject to subject, in a case where the parameters used for the behavior detection are uniformly set, the accuracy of behavior detection may be lowered.

The present disclosure has been made in view of such a situation, and it is desirable to improve the accuracy of behavior detection.

Solution to Problem

An information processing apparatus according to an embodiment of the present disclosure includes processing circuitry that sets a behavior detection parameter corresponding to a behavior of a subject based on input information corresponding to characteristics of a subject in an image, and detects a behavior of the subject based on the set behavior detection parameter and a posture of the subject in the image.

An information processing method according to an embodiment of the present disclosure being executed by an information processing apparatus including processing circuitry includes setting, by the processing circuitry, a behavior detection parameter based on input information corresponding to characteristics of a subject in an image and detecting, by the processing circuitry, a behavior of the subject based on the set behavior detection parameter and a posture of the subject in the image.

A non-transitory computer readable medium having stored thereon a program according to an embodiment of the present disclosure that when executed by processing circuitry of a computer causes the processing circuitry to implement a method including setting, by the processing circuitry, a behavior detection parameter based on input information corresponding to characteristics of a subject in an image and detecting, by the processing circuitry, a behavior of the subject based on the set behavior detection parameter and a posture of the subject in the image.

In the present disclosure, a behavior detection parameter used for detecting a behavior of a subject is set on the basis of input information associated with the subject in the image, and the behavior of the subject is detected on the basis of the behavior detection parameter that has been set and a posture of the subject in the image.

Advantageous Effects of Invention

According to the present disclosure, it may be possible to improve accuracy of behavior detection.

In addition, the effects described herein are not necessarily limited, and any of the effects described in the present disclosure may be obtained.

BRIEF DESCRIPTION OF DRAWINGS

FIG. 14 is a diagram illustrating an example of a parameter table.

DESCRIPTION OF EMBODIMENTS

Figure 1:
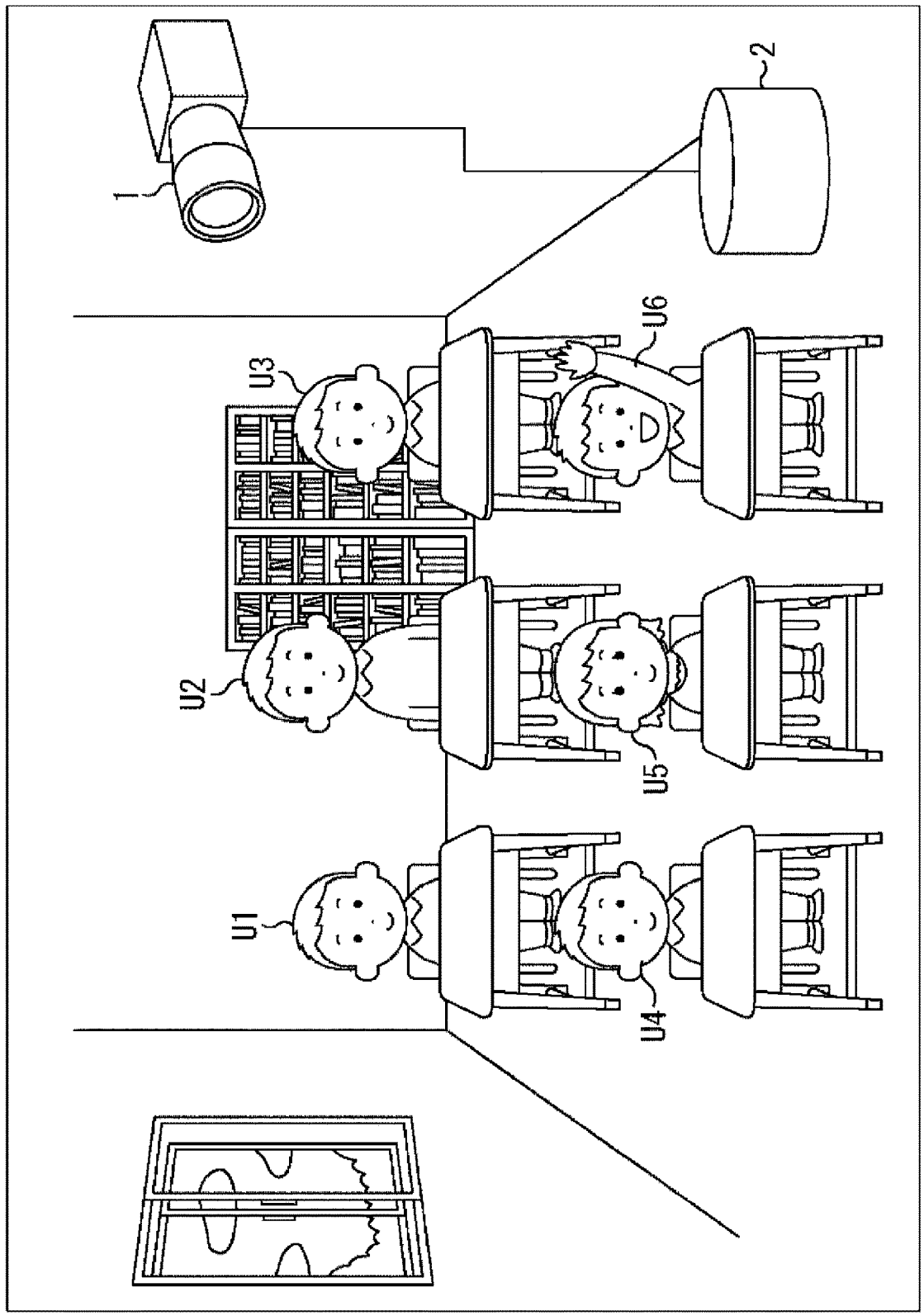
FIG. 1 is a diagram illustrating an overview of an imaging system according to an embodiment of the present disclosure.

Hereinafter, modes (hereinafter, referred to as embodiments) for implementing the present disclosure will be described. Note that the description will be made in the following order.

1. Problems in Lecture Capturing System in Related Art
2. Configuration of Imaging System According to Embodiment of Present Disclosure
3. First Embodiment (Basic Configuration and Operation)
4. Second Embodiment (Configuration for Age/Gender Estimation and Person Identification and Operation)
5. Third Embodiment (UI Display Example for Managing Parameter Table)
6. Modified Example
7. Configuration Example of Computer
8. Application Example 1. Problems in Lecture Capturing System in Related Art In recent years, there has been provided a lecture capturing system that records contents of a lecture at a school such as a university and realizes listening to the lecture at a remote location. In the lecture capturing system, in the case of imaging an auditor, a behavior of the auditor is detected, and a camera work is controlled. For example, if one of the auditors stands up, an image switching the camera work such as enlarging the auditor and imaging is recorded according to the behavior of the auditor.

In the camera work at this time, the person watching the image observes the behavior of the auditor by visual observation and manually switches the camera work on the basis of the observation result. If the behavior of the auditor which is necessary to switch the camera work can be automatically detected from the image, it may be possible to realize reduction in the number of observers and automatic control of the camera work.

The behavior detection for the auditor is performed on the basis of the posture detection result for the auditor and the threshold parameters (hereinafter, referred to as the behavior detection parameters) used for the behavior detection. The threshold parameters correspond to certain threshold values for certain behaviors.

For example, in the case of detecting the standing motion of the auditor, a minimum height position at which a face or a shoulder can exist during the standing, a highest height position at which a face or a shoulder can exist during the sitting, a difference (distance) between the two height positions, and the like are used as the behavior detection parameters.

The behavior of the subject can be detected by comparing the result of the posture detection of the auditor with the behavior detection parameter such as determining whether or not the current height position of the face obtained by the posture detection of the auditor is higher than the highest height position at which the face or shoulder can exist during the sitting of the behavior detection parameters.

In the above example, the behavior detection parameter for detecting the standing is described, but it is necessary to prepare completely different parameters depending on the type of the detected behavior.

The behavior detection parameters are set in advance by a system designer or set by a user (contractor who undertakes the setting of the system, or the like) at the time of using the system, but there were the following problems in each case.

(Problem 1)

The ages of auditors who are targets of imaging in lecture recording have a range of, for example, seven to twenty-two years old, and there is a difference in physical characteristics including height from age to age. For this reason, in a case where the parameters are uniformly set in advance, the accuracy of behavior detection may be lowered.

(Problem 2)

Since the parameters necessary for each type of behaviors to be detected are different, in a case where the parameter is set by the user, the amount of information input by the user becomes very large, and thus, there is a possibility that operating thereof becomes not easy.

Therefore, the configuration and operations of the system for solving the above problems will be described below.

2. Configuration of Imaging System According to Embodiment of Present Disclosure FIG. 1 is a diagram illustrating an overview of an imaging system according to an embodiment of the present disclosure.

The imaging system is configured as a lecture capturing system, and is installed in a classroom, auditorium, or the like where a lecturer (not illustrated) gives lectures to a plurality of auditors U1 to U6.

FIG. 1 illustrates that six auditors U1 to U6 listen to a lecture in the lecture room (classroom).

The imaging apparatus 1 is installed in the lecture room and captures an image with the angle of view in which all the auditors U1 to U6 are viewed. The captured image is output to the information processing apparatus 2.

The information processing apparatus 2 detects the behavior of each of the auditors U1 to U6 on the basis of the image from the imaging apparatus 1 and controls the imaging apparatus 1 on the basis of the detection result.

Figure 2:
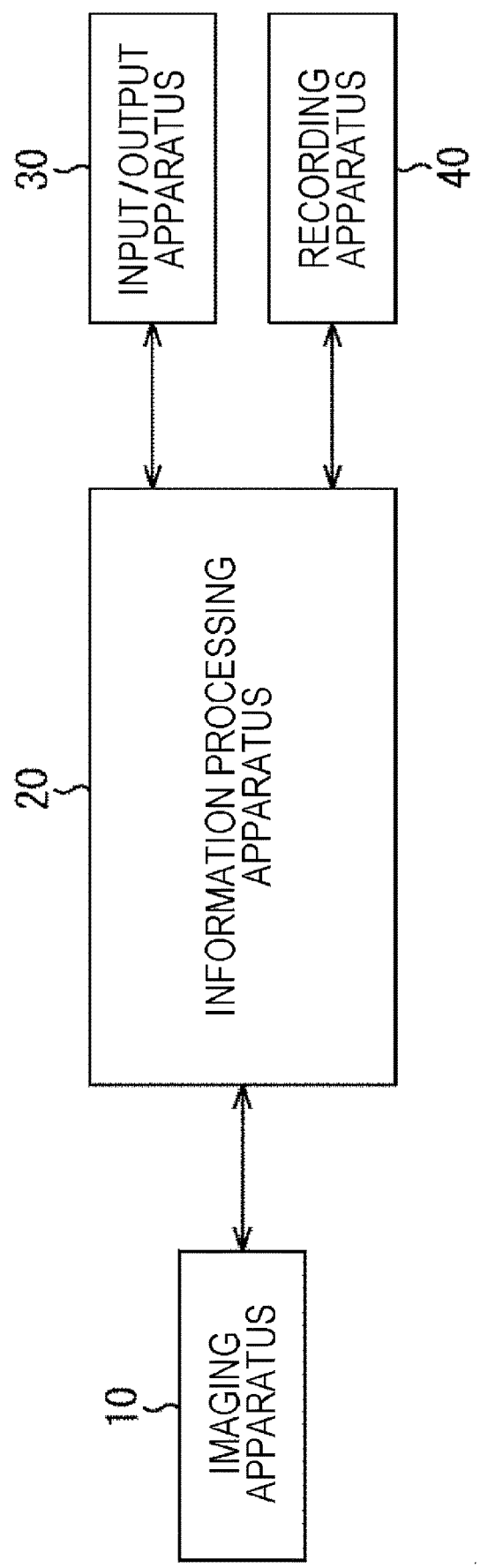
FIG. 2 is a block diagram illustrating a configuration example of the imaging system.

FIG. 2 is a block diagram illustrating a configuration example of an imaging system.

The imaging system in FIG. 2 includes the imaging apparatus 10, the information processing apparatus 20, the input/output apparatus 30, and the recording apparatus 40.

The imaging apparatus 10 and the information processing apparatus 20 correspond to the imaging apparatus 1 and the information processing apparatus 2 in FIG. 1.

For example, the imaging apparatus 10 is configured as a PTZ camera capable of optically and electronically zooming while having a function of mechanically panning and tilting. The number of imaging apparatuses 10 is not limited to one, and a plurality of imaging apparatuses may be provided.

The information processing apparatus 20 may be configured with dedicated hardware having the functions or may be configured with a general computer in which each function is realized by software. In addition, the imaging apparatus 10 and the information processing apparatus 20 may not be separately configured but may be integrally configured as one apparatus.

The input/output apparatus 30 is configured with a keyboard and a mouse for receiving a user's operation, a display having a display function, and the like. This display may be provided with a touch panel function. The input/output apparatus 30 receives an instruction based on the user's operation and outputs the instruction to the information processing apparatus 20. In addition, the input/output apparatus 30 presents various types of information supplied from the information processing apparatus 20 to the user.

The input/output apparatus 30 and the information processing apparatus 20 may not be separately configured but may be integrally configured as one apparatus. In addition, the input/output apparatus 30 may be connected to the information processing apparatus 20 via a network.

The recording apparatus 40 records various types of information supplied from the information processing apparatus 20. The information recorded in the recording apparatus 40 is read by the information processing apparatus 20 as necessary. As will be described in detail later, a parameter table in which behavior detection parameters are registered in association with each individual auditor is recorded in the recording apparatus 40.

The recording apparatus 40 and the information processing apparatus 20 may not be separately configured but may be integrally configured as one apparatus. In addition, the recording apparatus 40 may be connected to the information processing apparatus 20 via a network.

3. First Embodiment (Example of Functional Configuration of Information Processing Apparatus)

Figure 3:
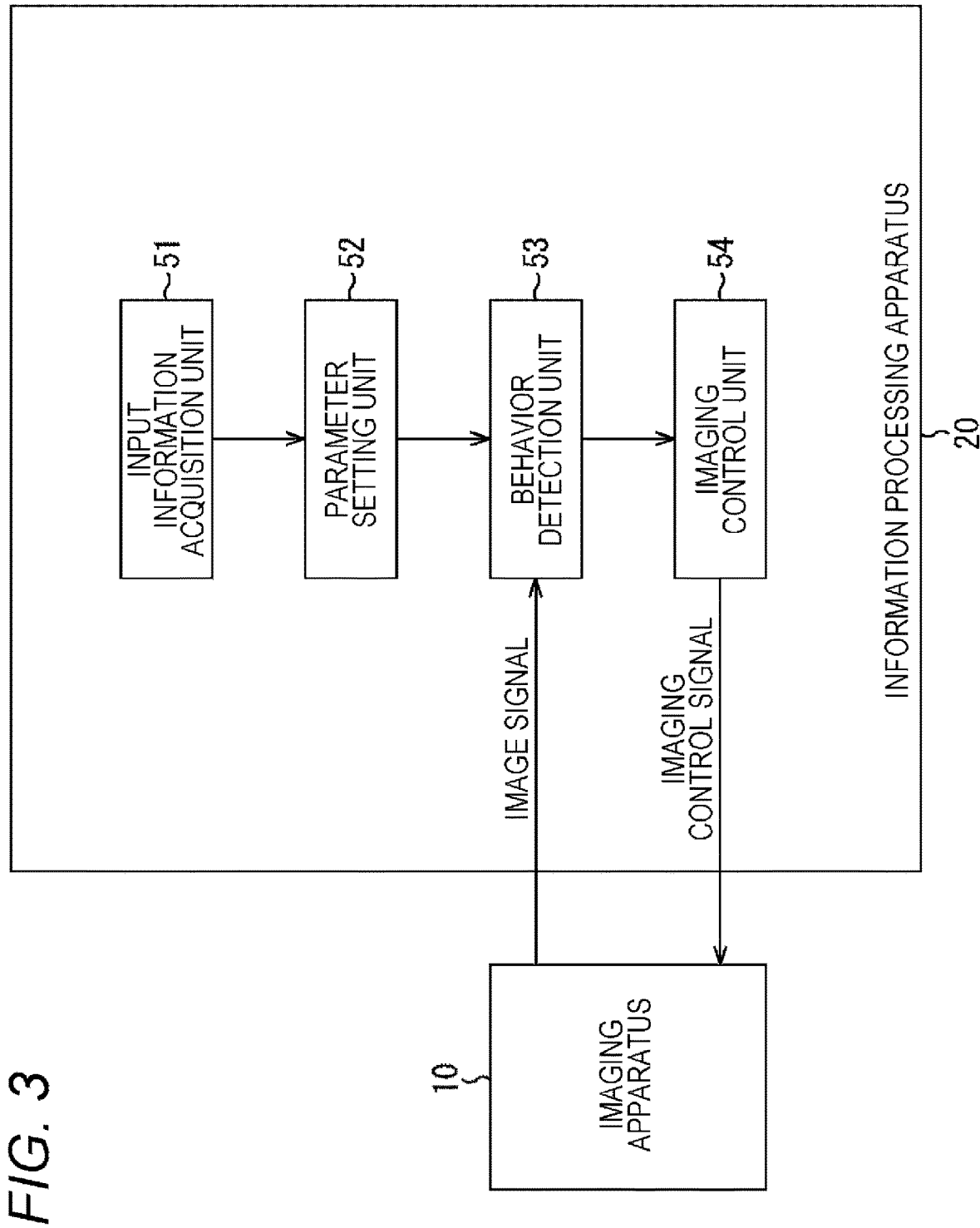
FIG. 3 is a block diagram illustrating a functional configuration example of an information processing apparatus according to a first embodiment.

FIG. 3 is a block diagram illustrating a functional configuration example of the information processing apparatus according to the first embodiment.

The information processing apparatus 20 of FIG. 3 includes an input information acquisition unit 51, a parameter setting unit 52, a behavior detection unit 53, and an imaging control unit 54.

The input information acquisition unit 51 acquires input information associated with the subject in the image input to the information processing apparatus 20 and supplies the input information to the parameter setting unit 52. The input information is acquired from the image signal indicating the image captured by the imaging apparatus 10 or acquired from the information input via the UI presented by the input/output apparatus 30 or the information recorded in the recording apparatus 40.

The parameter setting unit 52 sets the behavior detection parameters used for detecting the behavior of the subject in the image represented by the image signal from the imaging apparatus 10 on the basis of the input information from the input information acquisition unit 51 and supplies the behavior detection parameters to the behavior detection unit 53.

The behavior detection unit 53 detects the behavior of the subject on the basis of the behavior detection parameter from the parameter setting unit 52 and the posture of the subject in the image represented by the image signal from the imaging apparatus 10. The detection result of the behavior of the subject is supplied to the imaging control unit 54.

The imaging control unit 54 controls the imaging apparatus 10 according to the imaging control signal. Specifically, on the basis of the detection result of the behavior of the subject from the behavior detection unit 53, the imaging angle of view of the imaging apparatus 10 is controlled, and the range in which the image captured by the imaging apparatus 10 is cut out is controlled.

(Imaging Apparatus Control Process)

Figure 4:
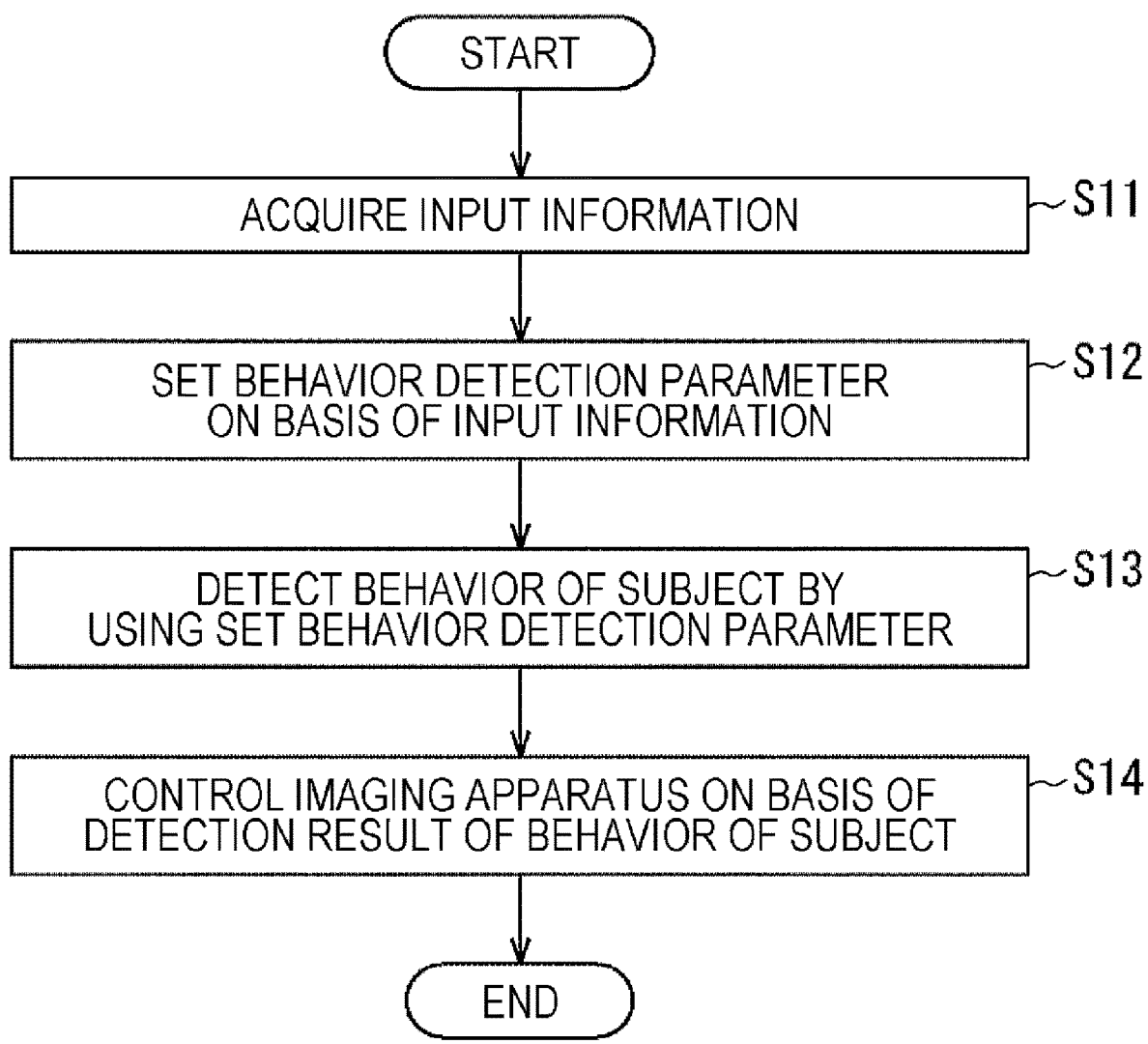
FIG. 4 is a flowchart illustrating an imaging apparatus control process.

Next, an imaging apparatus control process performed by the information processing apparatus 20 will be described with reference to the flowchart of FIG. 4.

In step S11, the input information acquisition unit 51 acquires input information. The input information is, for example, subject information associated with a subject (a subject which is a target of behavior detection) in an image captured by the imaging apparatus 10. Specifically, the subject information (input information) is information indicating an attribute of the subject and information associated with physical characteristics of the subject. The information indicating the attribute of the subject is, for example, the age, gender, race, dominant hand, hair style, color of hair, presence or absence of wearing eyeglasses, and the like of the subject. In addition, the information indicating the physical characteristics of the subject is, for example, the height, weight, sitting height of the subject, the lengths of the arm or leg, the length between the joints of the arm and leg, and the like.

In step S12, the parameter setting unit 52 sets the behavior detection parameters for the subject who is a target of the behavior detection on the basis of the acquired input information (subject information). The behavior detection parameters may be information associated with the physical characteristics of the subject in the image or information associated with the motion prediction of the subject. The behavior detection parameters are parameters optimized for each subject, and in a case where there are a plurality of subjects in the image, the behavior detection parameters are set for each subject.

In step S13, the behavior detection unit 53 detects the behavior of the subject who is a target of the behavior detection by using the set behavior detection parameter.

In step S14, the imaging control unit 54 controls the imaging apparatus 10 on the basis of the detection result of the behavior of the subject.

According to the above processes, since the behavior detection parameters optimized for the subject who is a target of the behavior detection are set, even if the physical characteristics such as height and physique are different for each subject, the accuracy of the behavior detection can be improved.

As a result, for example, in the lecture capturing system, it may be possible to realize highly accurate automatic control of the camera work such as accurately switching the camera work.

In the above description, the basic configuration and operations of the embodiment of the present disclosure have been described. Hereinafter, specific configuration and operations for performing the behavior detection of the auditor in the imaging system (lecture capturing system) in FIG. 1 will be described.

4. Second Embodiment (Functional Configuration Example of Information Processing Apparatus) FIG. 5 is a block diagram illustrating a functional configuration example of the information processing apparatus according to a second embodiment.

Figure 5:
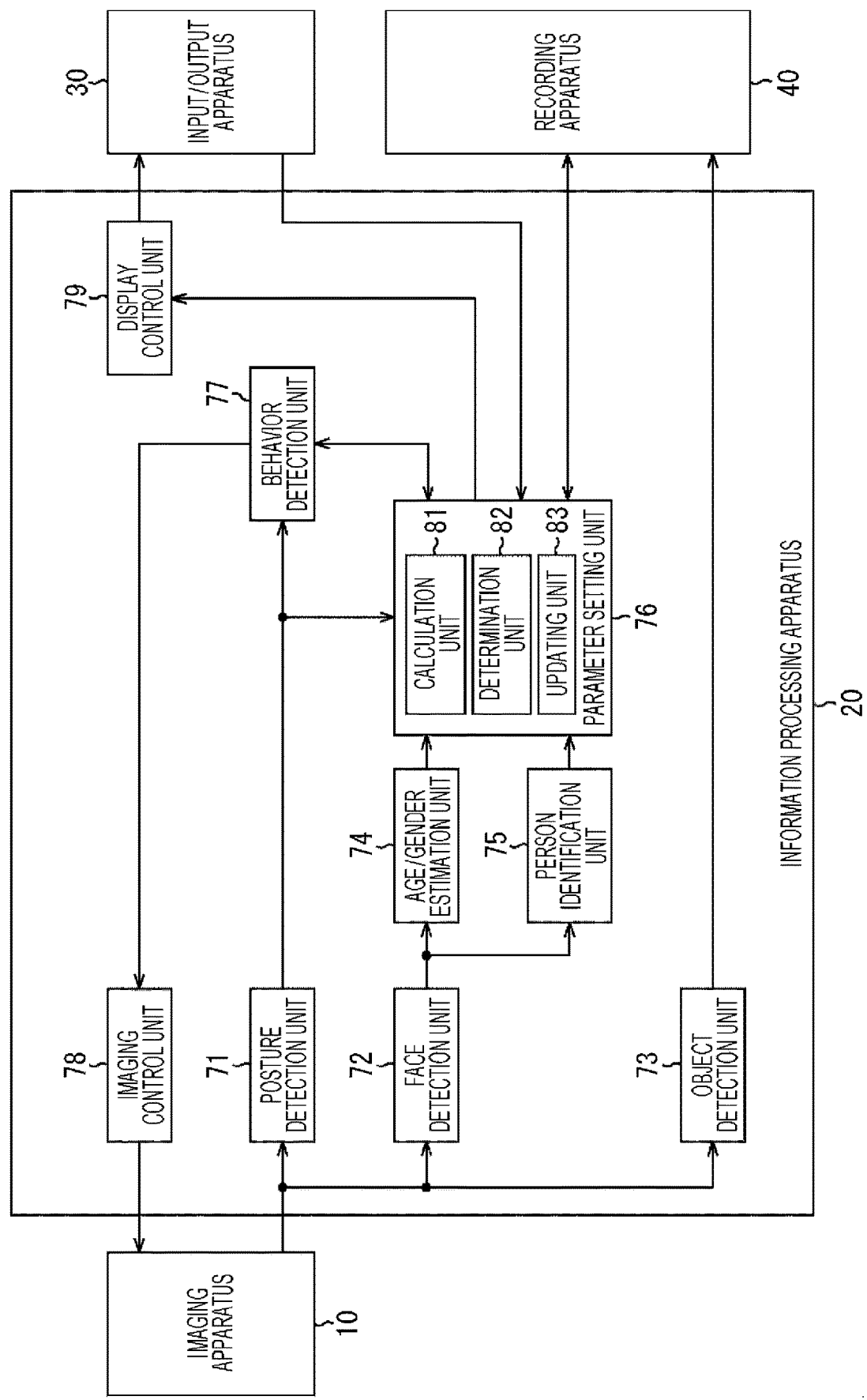
FIG. 5 is a block diagram illustrating a functional configuration example of an information processing apparatus according to a second embodiment.

The information processing apparatus 20 of FIG. 5 includes a posture detection unit 71, a face detection unit 72, an object detection unit 73, an age/gender estimation unit 74, a person identification unit 75, a parameter setting unit 76, a behavior detection unit 77, an imaging control unit 78, and a display control unit 79.

The posture detection unit 71 detects the posture as the information associated with the physical characteristics of the auditor (subject) in the image from the imaging apparatus 10 and supplies the posture information indicating the detected posture to the parameter setting unit 76 and the behavior detection unit 77. The posture information may be information including the joint information indicating joints of a person appearing in the image and the skeleton information connecting pieces of the joint information with each other or may be information including only one of the information. In addition, the posture information is not particularly limited to the above-described information, and the posture information may be information associated with a posture indicating the physical characteristics of the subject. The posture of the subject may represent the position in which the subject holds their body including their hands, arms, head and/or torso.

Figure 6:
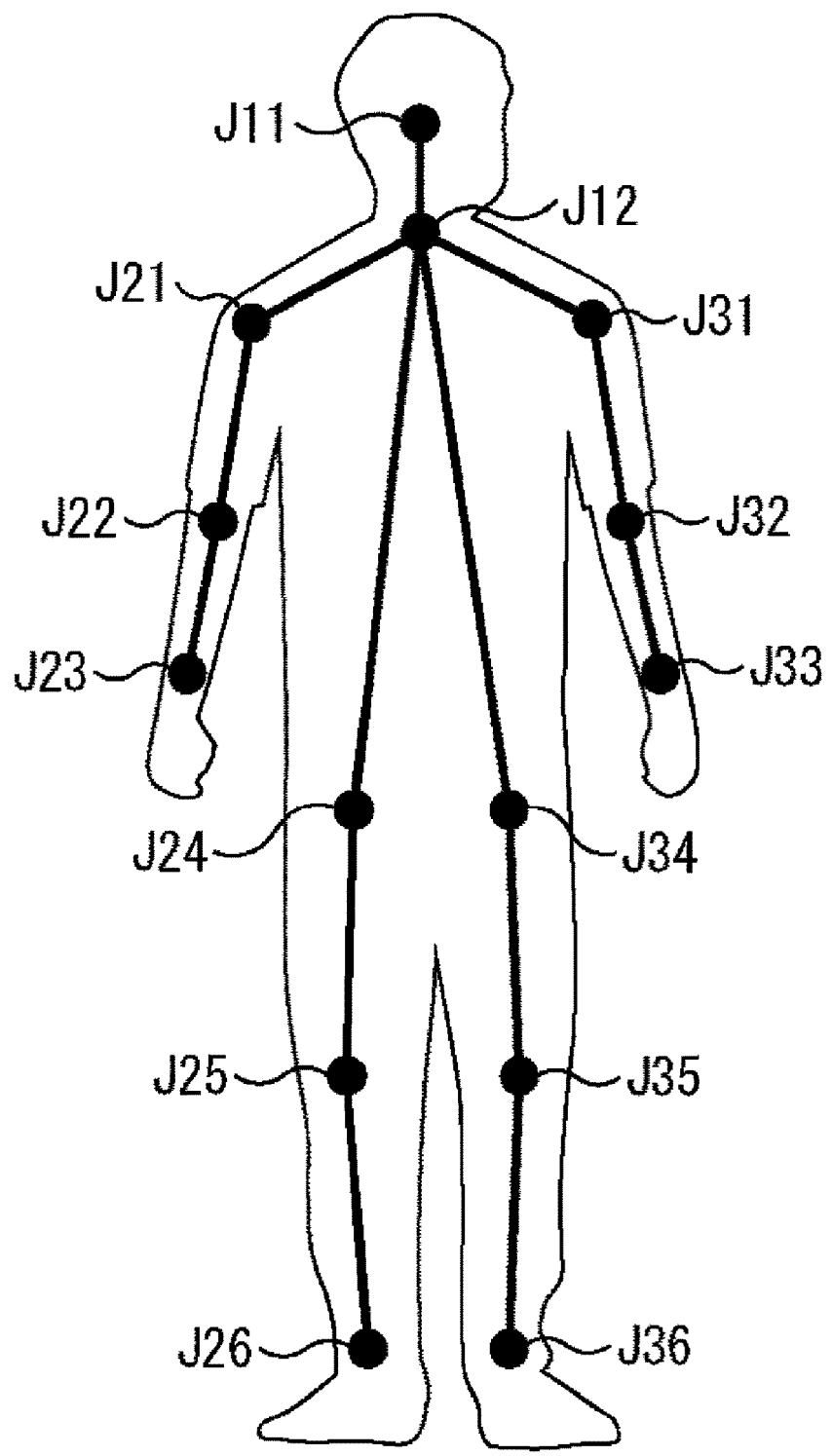
FIG. 6 is a diagram illustrating an example of posture information.

FIG. 6 is a diagram illustrating an example of the posture information.

In FIG. 6, fourteen pieces of joint information J11, J12, J21 to J26, and J31 to J36 are indicated by dots, and skeleton information connecting the pieces of the joint information is indicated by line segments connecting two points.

In the example of FIG. 6, the pieces of joint information J11 and J12 indicate the head and neck of the human body, respectively. The pieces of joint information J21 to J23 indicate the right shoulder, the right elbow, and the right wrist of the human body, respectively; and the pieces of joint information J24 to J26 indicate the right hip joint, the right knee, the right ankle of the human body, respectively. The pieces of joint information J31 to J33 indicate the left shoulder, the left elbow, and the left wrist of the human body, respectively; and the pieces of joint information J34 to J36 indicate the left hip joint, the left knee, and the left ankle of the human body, respectively.

Returning to the description of FIG. 5, the face detection unit 72 detects the face of the auditor in the image from the imaging apparatus 10, and supplies face information indicating the detected face to the age/gender estimation unit 74 and the person identification unit 75. The face information includes the position of the detected face in the image and the face image.

The object detection unit 73 detects an object in the image from the imaging apparatus 10 and outputs object information indicating the detected object to the recording apparatus 40. The object information includes the position of the detected object in the image and type information indicating the type of the object. The type of the object includes general objects in a lecture room such as a desk, a window, a bookshelf, a blackboard, and a wall, for example.

The age/gender estimation unit 74 estimates the age and gender of the auditor corresponding to the face information on the basis of the face information from the face detection unit 72. Age/gender information indicating the estimated age and gender is supplied to the parameter setting unit 76.

The person identification unit 75 calculates a personal characteristic quantity identifying the individual auditor corresponding to the face information on the basis of the face information from the face detection unit 72 and supplies the calculated personal characteristic quantity to the parameter setting unit 76. The personal characteristic quantity may be a characteristic quantity that is extracted from a single image (still image) such as Speed-Up Robust Features (SURF) or may be a characteristic quantity that is extracted from an image (moving image) and changing in the time direction such as a motion of a portion of the body (for example, a motion of the eyelids).

The parameter setting unit 76 sets behavior detection parameters of each individual auditor. The parameter setting unit 76 includes a calculation unit 81, a determination unit 82, and an updating unit 83.

On the basis of the age/gender information from the age/gender estimation unit 74, the calculation unit 81 calculates the behavior detection parameters according to the age and gender of the auditor corresponding to the age/gender information. Specifically, the calculation unit 81 calculates the behavior detection parameters by using average physical characteristics of persons of the estimated age and gender.

The determination unit 82 determines one of the behavior detection parameter calculated by the calculation unit 81 and the behavior detection parameter recorded in the recording apparatus 40 as the behavior detection parameter to be used for detection of an actual behavior on the basis of the personal characteristic quantity from the person identification unit 75.

Specifically, the determination unit 82 determines whether or not the behavior detection parameter associated with the auditor corresponding to the personal characteristic quantity from the person identification unit 75 is registered in the parameter table of the recording apparatus 40.

In a case where the behavior detection parameter associated with the auditor is registered in the parameter table, the determination unit 82 determines the behavior detection parameter registered in the parameter table as the behavior detection parameter actually used for detecting the behavior. The behavior detection parameter associated with the auditor can be said to be a parameter optimized for the auditor.

On the other hand, in a case where the behavior detection parameter associated with the auditor is not registered in the parameter table, the determination unit 82 determines the behavior detection parameter calculated by the calculation unit 81 as the behavior detection parameter actually used for detecting the behavior. The behavior detection parameter calculated by the calculation unit 81 can also be said to be a parameter optimized for the auditor.

The behavior detection parameter determined in this manner is supplied to the behavior detection unit 77 as a parameter optimized for each individual auditor.

The updating unit 83 updates the behavior detection parameters of the auditor who is a target of the behavior detection on the basis of the posture information from the posture detection unit 71 and the behavior information (information indicating the detection result of the behavior) from the behavior detection unit 77. The updated behavior detection parameter is reflected on the parameter table of the recording apparatus 40, and the parameter table is updated.

The various types of information used in the processing in the parameter setting unit 76 and the process results are appropriately supplied to the recording apparatus 40 and the input/output apparatus 30 via the display control unit 79.

The behavior detection unit 77 detects at least one type of behavior of the auditor by using the posture information from the posture detection unit 71 and the behavior detection parameters from the parameter setting unit 76 (determination unit 82). The detected behavior of the auditor is an operation that the auditor can take during the lecture. Examples of behaviors that can be taken during the lecture include, for example, standing, bowing, raising a hand, sitting, moving forward, uttering (speaking), reading a textbook, writing a note or the like, dozing, casting a side glance, chatting (not uttering on the contents of a lecture but individual utterance not related to the lecture), and the like.

The behavior information indicating the detection result of the behavior together with the information (face information, personal characteristic quantity, and age/gender information) of the auditor which is a target of the behavior detection is supplied to the parameter setting unit 76 (updating unit 83) and is used for updating the behavior detection parameters (parameter table). The behavior information is also supplied to the imaging control unit 78.

The imaging control unit 78 controls the imaging apparatus 10 on the basis of the behavior information from the behavior detection unit 77. On the basis of the behavior information, the imaging control unit 78 zooms up, for example, the standing auditor or cuts out the range in which a plurality of auditors raising hands are reflected from the image.

The display control unit 79 controls display of various types of information from the parameter setting unit 76 on the display constituting the input/output apparatus 30.

(Behavior Detection Parameter Setting Process)

Figure 7:
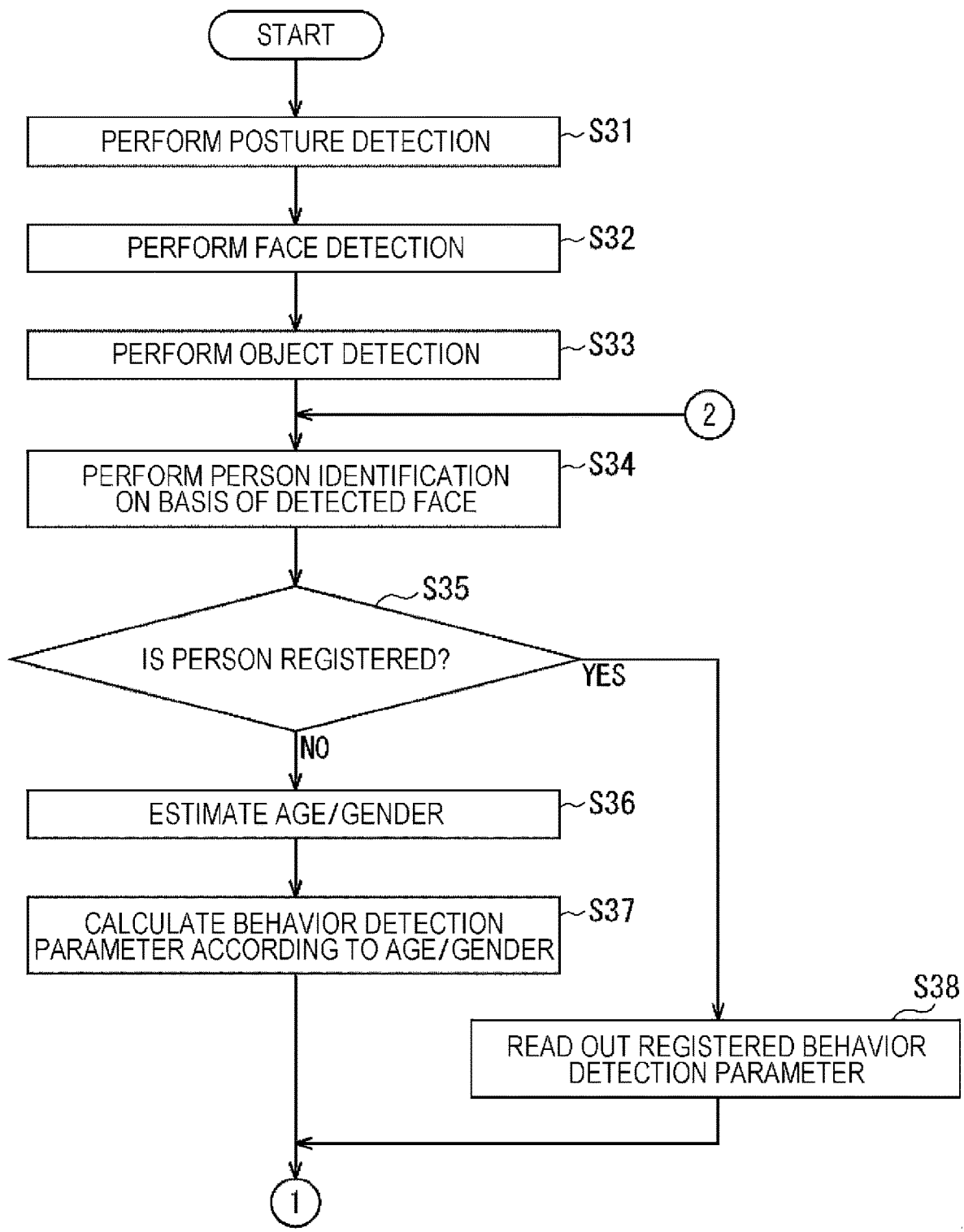
FIG. 7 is a flowchart illustrating a behavior detection parameter setting process.
Figure 8:
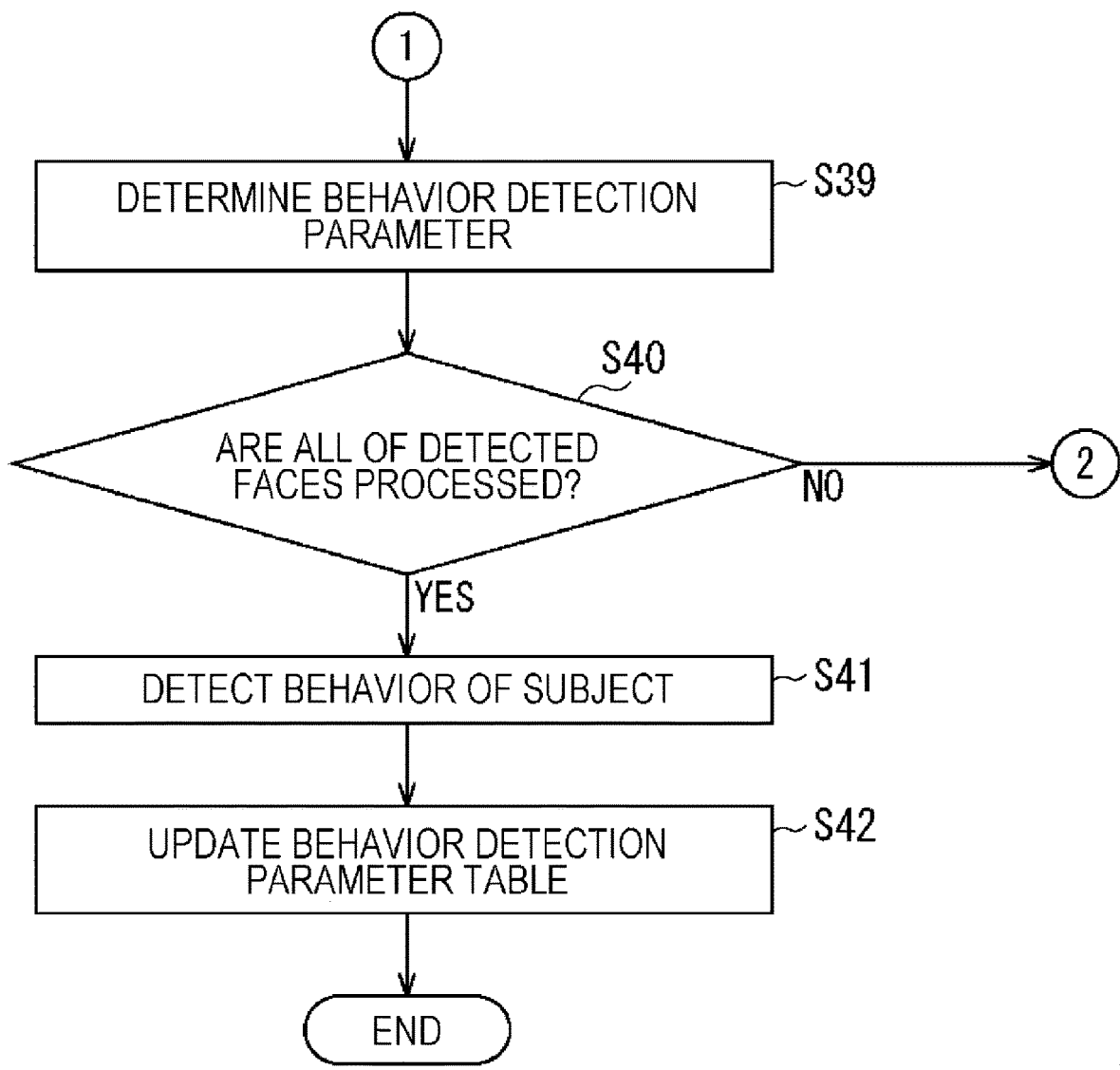
FIG. 8 is a flowchart illustrating a behavior detection parameter setting process.

Next, a behavior detection parameter setting process by the information processing apparatus 20 will be described with reference to the flowcharts of FIGS. 7 and 8.

Figure 9:
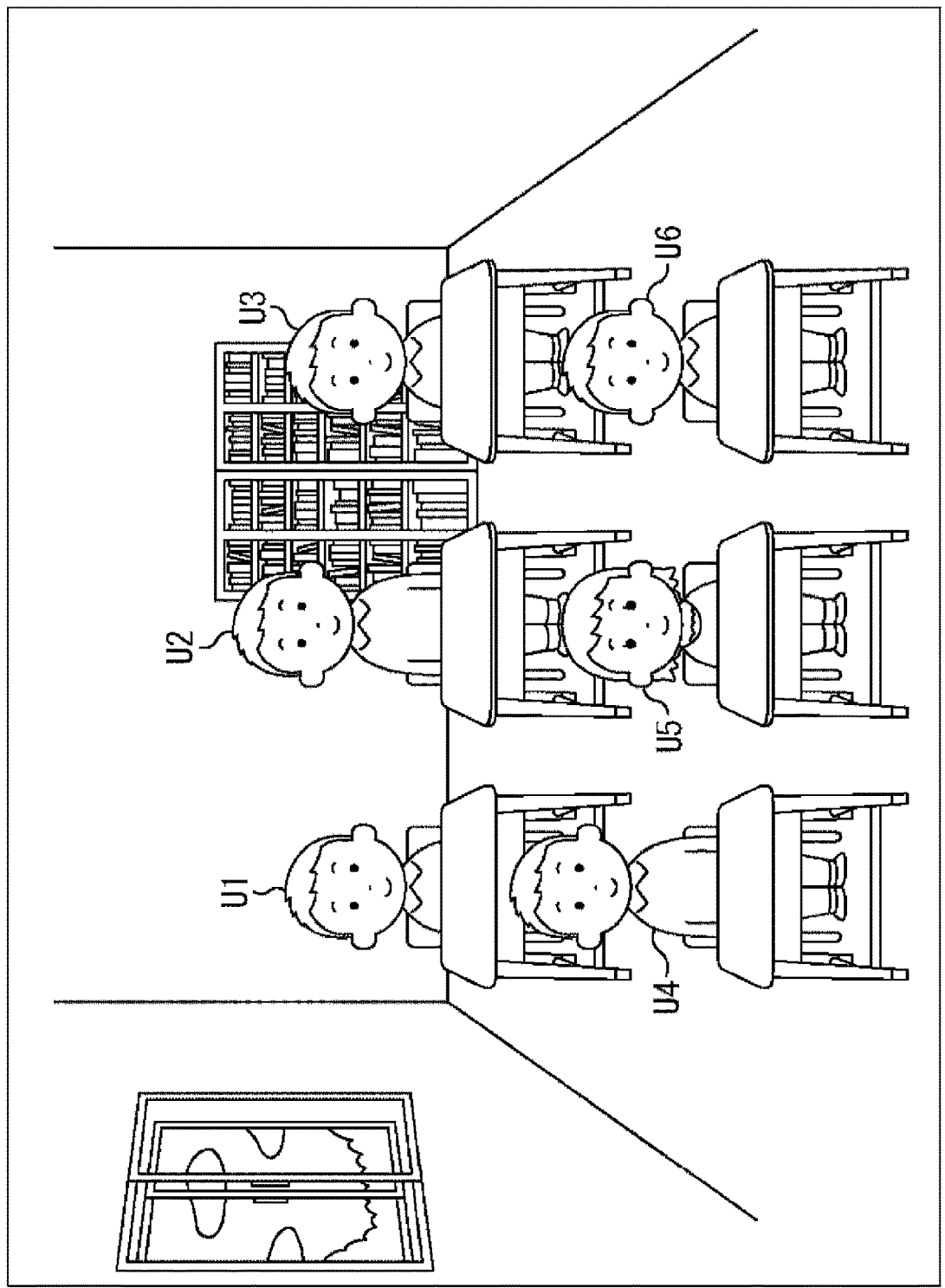
FIG. 9 is a diagram illustrating an example of an image in a lecture capturing system.

In this example, the behavior detection parameter setting process is executed on the image captured where the six auditors U1 to U6 listen to a lecture in the lecture room as illustrated in FIG. 9. In FIG. 9, the auditors U1, U3, U5, and U6 take seats, and the auditors U2 and U4 stand up.

In the following, an example where the standing motion is detected will be described.

If the image illustrated in FIG. 9 is supplied from the imaging apparatus 10 to the information processing apparatus 20, in step S31, the posture detection unit 71 detects the posture of the auditors U1 to U6 in the image from the imaging apparatus 10.

Figure 10:
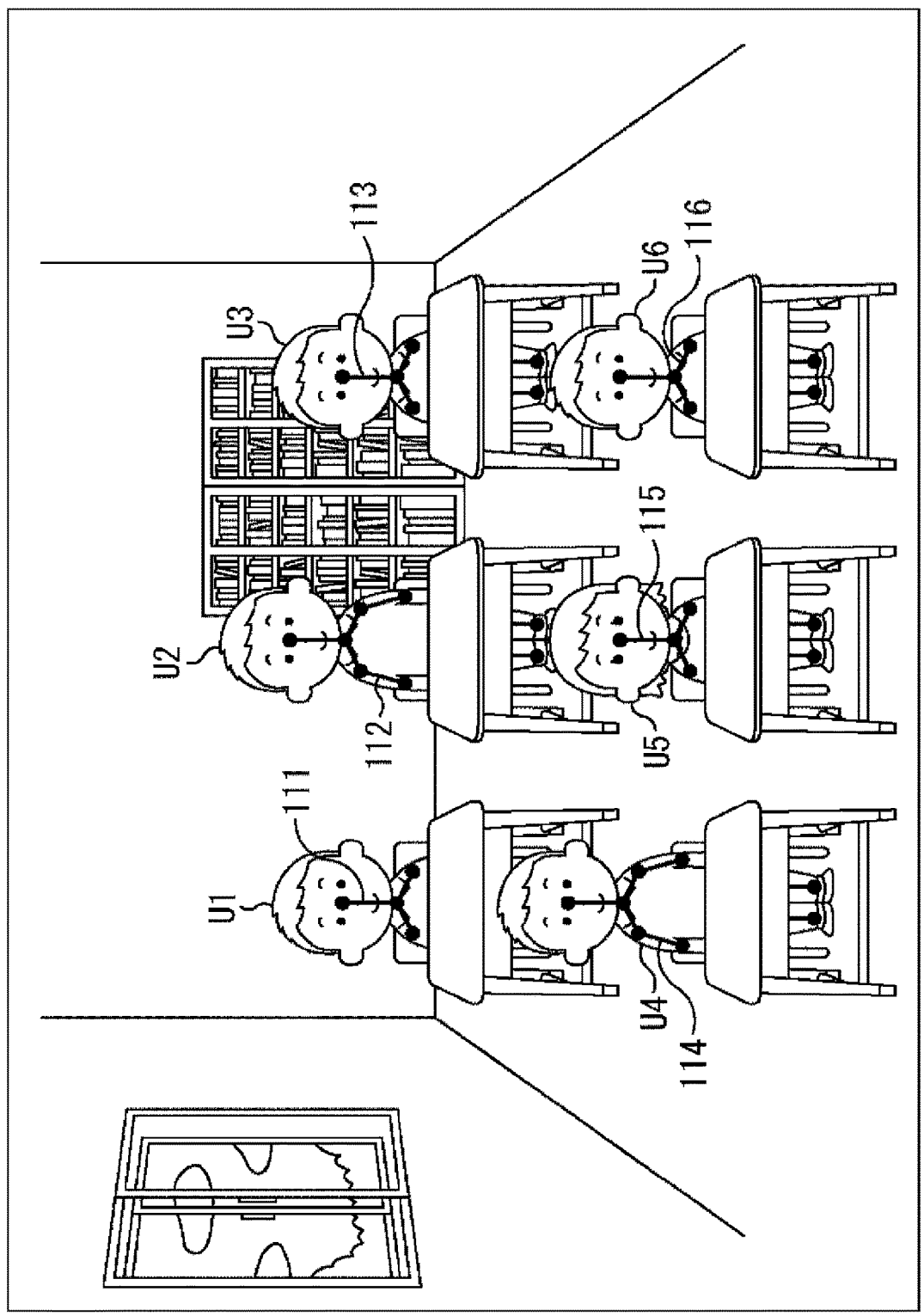
FIG. 10 is a diagram illustrating posture detection.

FIG. 10 is a diagram illustrating the posture detection of each of the auditors U1 to U6.

In FIG. 10, pieces of the posture information 111 to 116 including joint information and skeleton information are illustrated for the auditors U1 to U6, respectively. The joint information and the skeleton information constituting the posture information include information indicating which part of the body each corresponds to.

The posture information obtained in this manner is supplied to the parameter setting unit 76 and the behavior detection unit 77.

In step S32, the face detection unit 72 detects the faces of the auditors U1 to U6 in the image from the imaging apparatus 10.

Figure 11:
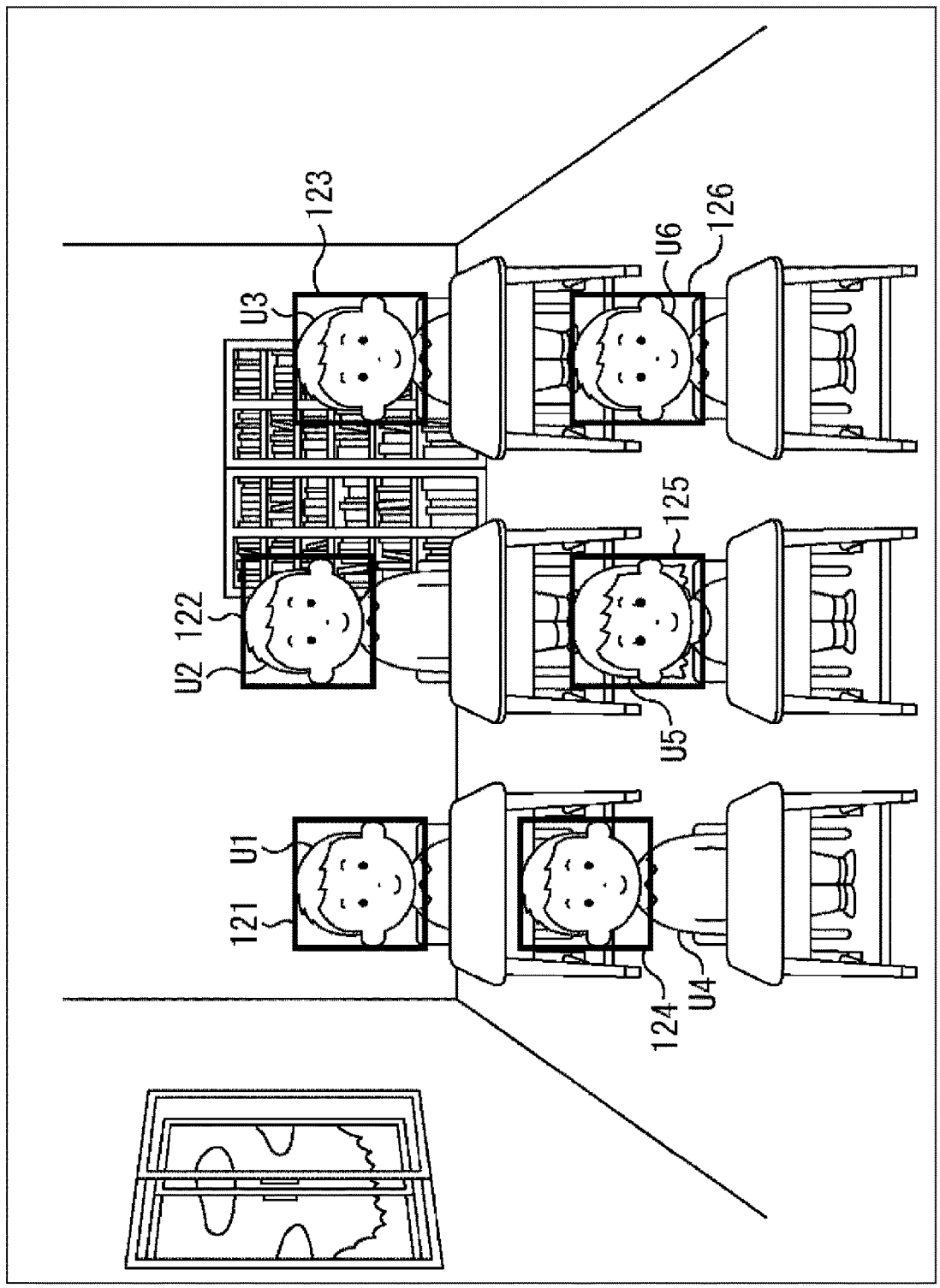
FIG. 11 is a diagram illustrating face detection.

FIG. 11 is a diagram illustrating the face detection of each of the auditors U1 to U6.

FIG. 11 illustrates frames 121 to 126 illustrating the faces of the detected auditors U1 to U6, respectively. In the example of FIG. 11, the face images and the positions of the auditors U1 to U6 enclosed by the frames 121 to 126 become the face information.

The face information obtained in this manner is supplied to the age/gender estimation unit 74 and the person identification unit 75.

In step S33, the object detection unit 73 detects an object in the image from the imaging apparatus 10.

Figure 12:
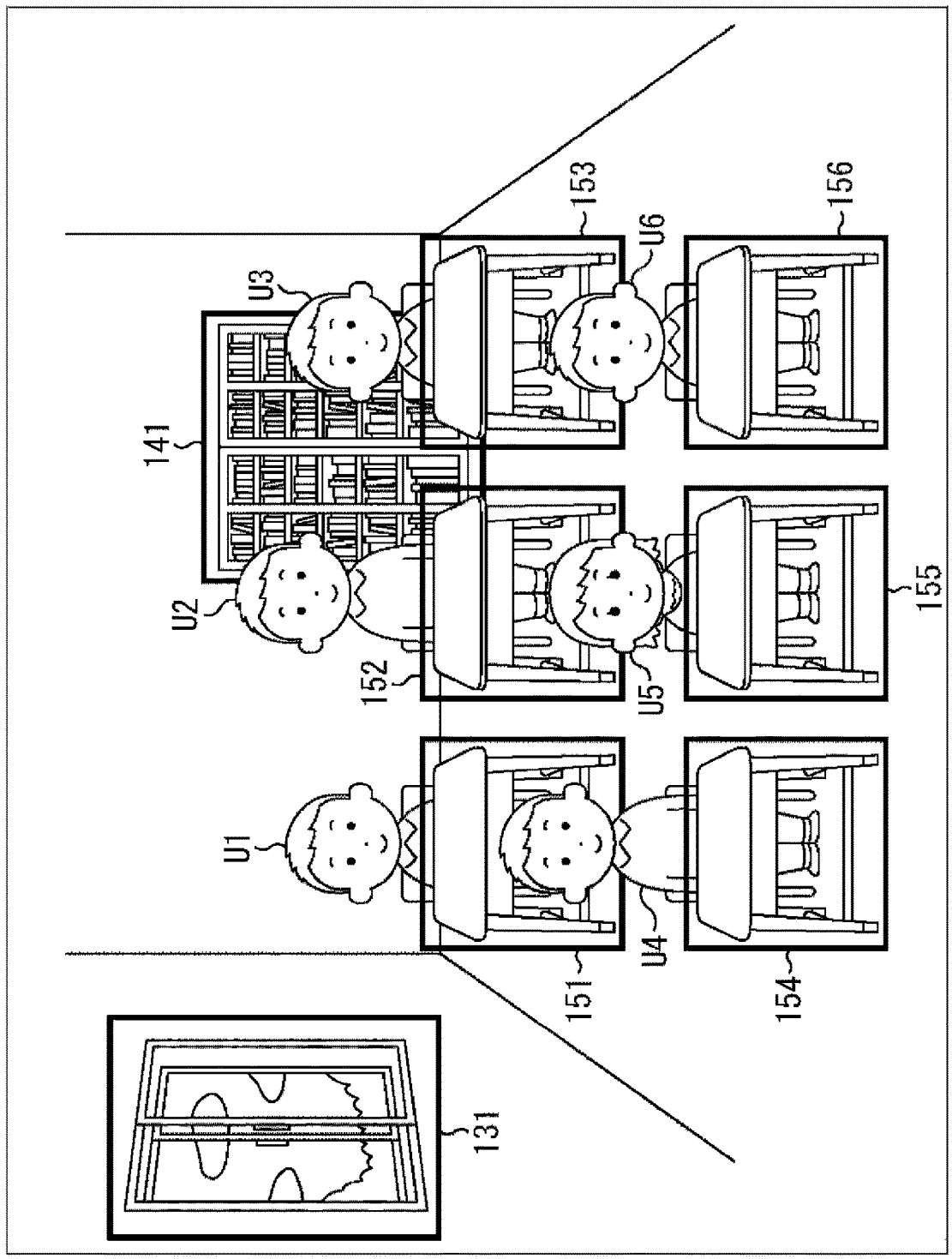
FIG. 12 is a diagram illustrating object detection.

FIG. 12 is a diagram illustrating object detection. Herein, it is assumed that a window, a bookshelf, and a desk are set as types of objects to be detected.

In FIG. 12, there are illustrated a frame 131 illustrating the detected window, a frame 141 illustrating the bookshelf, frames 151 to 156 indicating the desks at the seats of the auditors U1 to U6. In the example of FIG. 12, the type and the position of each of the objects enclosed by the frames 131, 141, 151 to 156 become the object information.

The object information obtained in this way is output to the recording apparatus 40.

Figure 13:
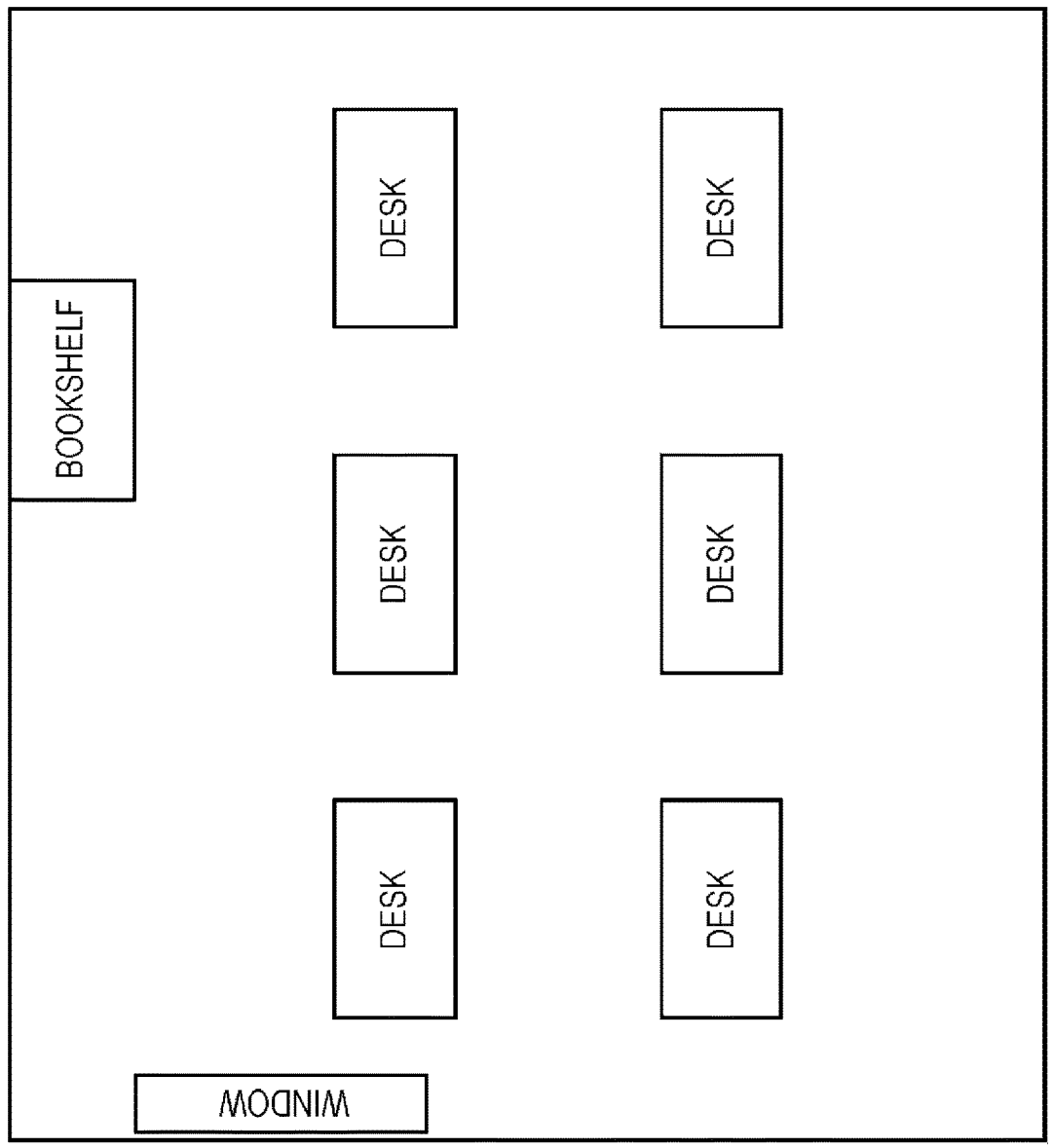
FIG. 13 is a diagram illustrating a position of an object.

In addition, the position of the object included in the object information may be a position on an image plane or a position on a three-dimensional space. For example, by acquiring three-dimensional information such as depth information of each object in the image from the imaging apparatus 10, the position of each object in the three-dimensional space is obtained. As a result, for example, as illustrated in FIG. 13, the object information including the positions of a window, a bookshelf, and desks when viewing the lecture room from the top is obtained.

In step S34, on the basis of the face information from the face detection unit 72, the person identification unit 75 performs identification of a person with respect to one of the detected faces and calculates a personal characteristic quantity.

In step S35, the person identification unit 75 determines whether or not the auditor corresponding to the calculated personal characteristic quantity is a person registered in the parameter table of the recording apparatus 40.

In a case where it is determined in step S35 that the person is not a registered person, the process proceeds to step S36, and the age/gender estimation unit 74 estimates the age and gender of the auditor on the basis of the face information from the face detection unit 72 and supplies the age/gender information to the parameter setting unit 76.

In step S37, the calculation unit 81 of the parameter setting unit 76 calculates the behavior detection parameters according to the age/gender of the auditor on the basis of the age/gender information from the age/gender estimation unit 74.

With respect to the behavior detection parameter, a reference value (default value) is set in advance for each type of the behaviors. A method of the behavior detection by using default values of behavior detection parameters is not particularly limited, and a known method can be used. For example, by using the detected height position of the face, the state of standing/sitting can be determined. In addition, by using the detected posture information, the stage of bowing and raising a hand can be determined. In addition, by using the detected posture information and the time information in which the state is maintained, for example, if the standing state is maintained for a certain period of time, the state of uttering can be determined. In this embodiment, the behavior detection parameter is calculated by adjusting the default value of the behavior detection parameter used for the behavior detection according to the age/gender of the auditor.

For example, in a case where the age/gender of the auditor U4 estimated on the basis of the face information of the auditor U4 is twelve years old/male, the behavior detection parameter for detecting the standing motion can be calculated by adjusting the default value for the operation on the basis of the average values of the height and sitting height of the twelve year old male Japanese. However, the behavior detection parameters calculated by using the age/gender are average values according to the age/gender, and may not absorb differences in physical characteristics between the individual auditors.

On the other hand, in a case where it is determined in step S35 that the person is a registered person, the process proceeds to step S38, and the determination unit 82 reads out the behavior detection parameter of the auditor registered in the parameter table of the recording apparatus 40.

FIG. 14 is a diagram illustrating an example of the parameter table.

The parameter table includes face information, name information, parameter (behavior detection parameter), personal characteristic quantity, and age/gender information for each auditor.

In the example of FIG. 14, the behavior detection parameters of the auditors U1, U2, U3, U5, and U6 are registered.

For example, the face information (face image) of the auditor U1, the name "OO Ichiro", the behavior detection parameters p11 and p12, the personal characteristic quantities f11 and f12, and 12/male of age/gender are registered for the auditor U1. Among the pieces of information, the face information, the name information, and the age/gender information are information used for displaying a parameter table management screen described later.

Note that, in the example of FIG. 14, the behavior detection parameter of the auditor U4 is not registered.

After step S37 or S38, in step S39, the determination unit 82 determines the behavior detection parameter actually used for detecting the behavior.

For example, in a case where the processing target is the auditor U4, since the behavior detection parameter of the auditor U4 is not registered in the parameter table, the behavior detection parameter corresponding to the age/gender calculated in the step S37 is determined as the behavior detection parameter used for actually detecting the behavior.

In addition, in a case where the processing target is any one of the auditors U1, U2, U3, U5, and U6, since the behavior detection parameters of the auditors are registered in the parameter table, the behavior detection parameters read out in step S38 are determined to be behavior detection parameters which are actually used for detecting the behavior.

The determined behavior detection parameter is supplied to the behavior detection unit 77.

In step S40, on the basis of the face information from the face detection unit 72, the person identification unit 75 determines whether or not processing has been performed for all the detected faces.

In a case where it is determined that all of the detected faces have not been processed, the process returns to step S34, and the processes of steps S34 to S39 are repeated.

On the other hand, in a case where it is determined that all the detected faces have been processed, the process proceeds to step S41, where the behavior of the auditor (subject) is detected by using the posture information from the posture detection unit 71 and the behavior detection parameter from the determination unit 82.

That is, the behavior of the auditors U1, U2, U3, U5, and U6 is detected by using behavior detection parameters registered in the parameter table, and the behavior of the auditor U4 is detected by using the behavior detection parameters calculated according to the age/gender.

The behavior information indicating the detection result of the behavior is supplied to the updating unit 83 together with the information (face information, personal characteristic quantity, and age/gender information) of the auditor who is a target of the behavior detection.

In step S42, the updating unit 83 updates the parameter table of the recording apparatus 40 on the basis of the posture information from the posture detection unit 71 and the behavior information from the behavior detection unit 77.

For example, in a case where the standing of the auditor U4 is detected, the joint information of the auditor U4 at the time of standing operation and the like are registered as the behavior detection parameters used for detecting the standing of the auditor U4 in the parameter table. At this time, the face information, the personal characteristic quantity, and the age/gender information of the auditor U4 are also registered in the parameter table.

In addition, in a case where the behavior of the auditor registered in the parameter table is detected, the behavior detection parameters of the auditor may be updated on the basis of the posture information acquired at this time.

In this manner, the behavior detection parameters optimized for each individual auditor are registered in the parameter table. Thus, in the next frame of the image, for example, even for the auditor U4, it may be possible to perform the behavior detection using the behavior detection parameters corresponding to the physical characteristics of the auditor U4.

According to the above processes, since the behavior detection parameters optimized for each individual auditor are set, even if the physical characteristics such as height and physique are different for each auditor in the lecture capturing system, the accuracy of the behavior detection can be improved.

In addition, since it is unnecessary for the user to input and set the behavior detection parameters for each type of behavior to be detected, the operating of the system can be simplified.

In the above description, an example where only the standing motion is detected has been described, but the detection of plural types of behaviors may be performed at the same time.

Hereinafter, a configuration for enabling the user to easily manage the parameter table in the imaging system (lecture capturing system) of FIG. 1 will be described.

5. Third Embodiment

Figure 15:
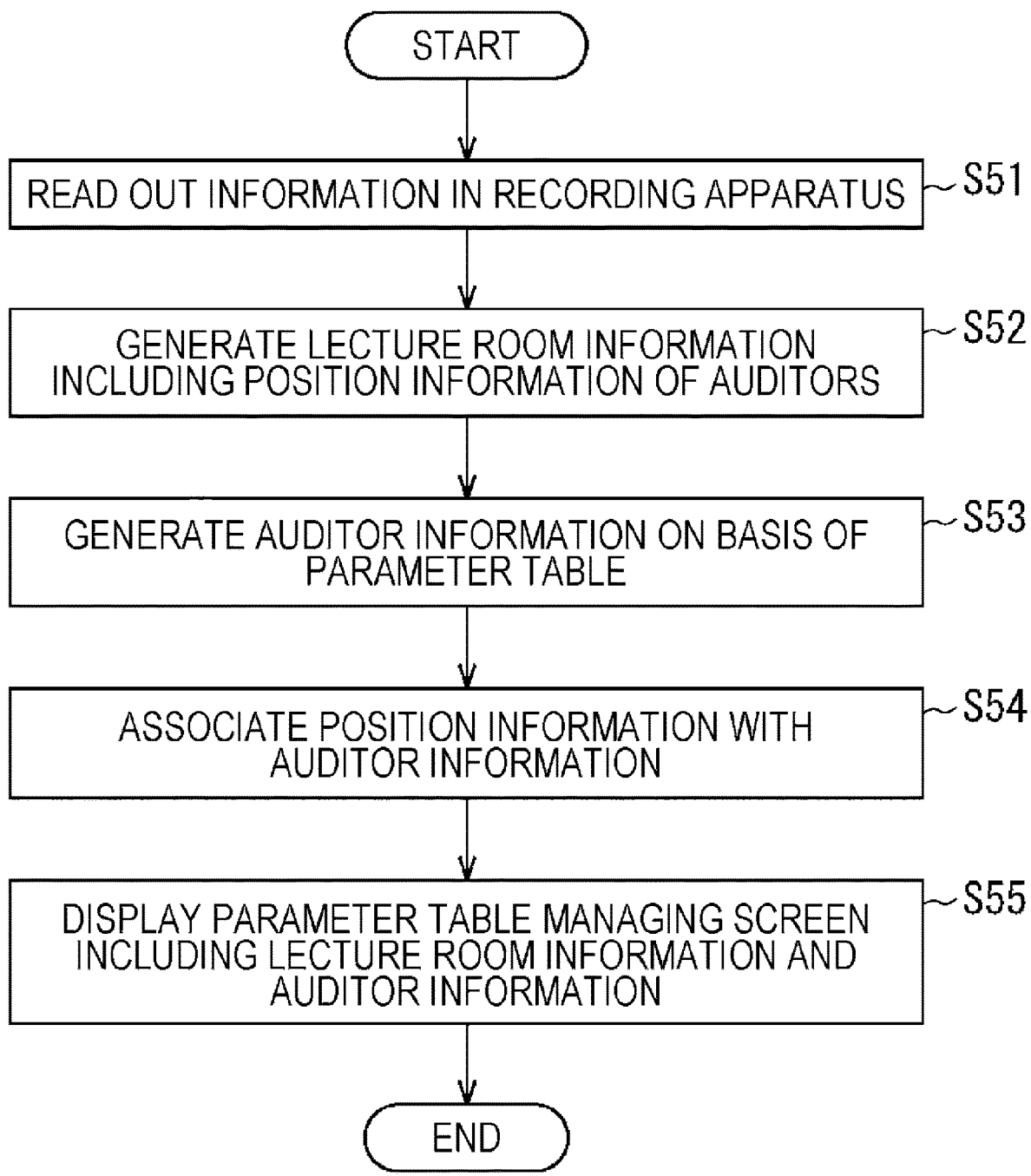
FIG. 15 is a flowchart illustrating a display process of a parameter table management screen.

First, a display process of the parameter table management screen which is a UI for managing the parameter table will be described with reference to a flowchart of FIG. 15.

In step S51, the parameter setting unit 76 reads out various types of information recorded in the recording apparatus 40 and supplied from the information processing apparatus 20.

In step S52, on the basis of the object information and the posture information of the auditor among the various types of information read out from the recording apparatus 40, the parameter setting unit 76 acquires the lecture room information including the position information indicating the positions of the auditors in the lecture room. The lecture room information includes the position information of various different objects based on the object information and the position information of the auditor based on the posture information.

In step S53, the parameter setting unit 76 generates auditor information on the basis of the parameter table read from the recording apparatus 40. The auditor information includes face information, name information, and age/gender information of the parameter table.

In step S54, the parameter setting unit 76 associates the position information of the auditor included in the lecture room information with the auditor information. The association of the position information with the auditor information is performed by using the personal characteristic quantity of each auditor.

The lecture room information and auditor information thus obtained are supplied to the display control unit 79.

In step S55, the display control unit 79 displays a parameter table management screen including the lecture room information and the auditor information on a display constituting the input/output apparatus 30.

Figure 16:
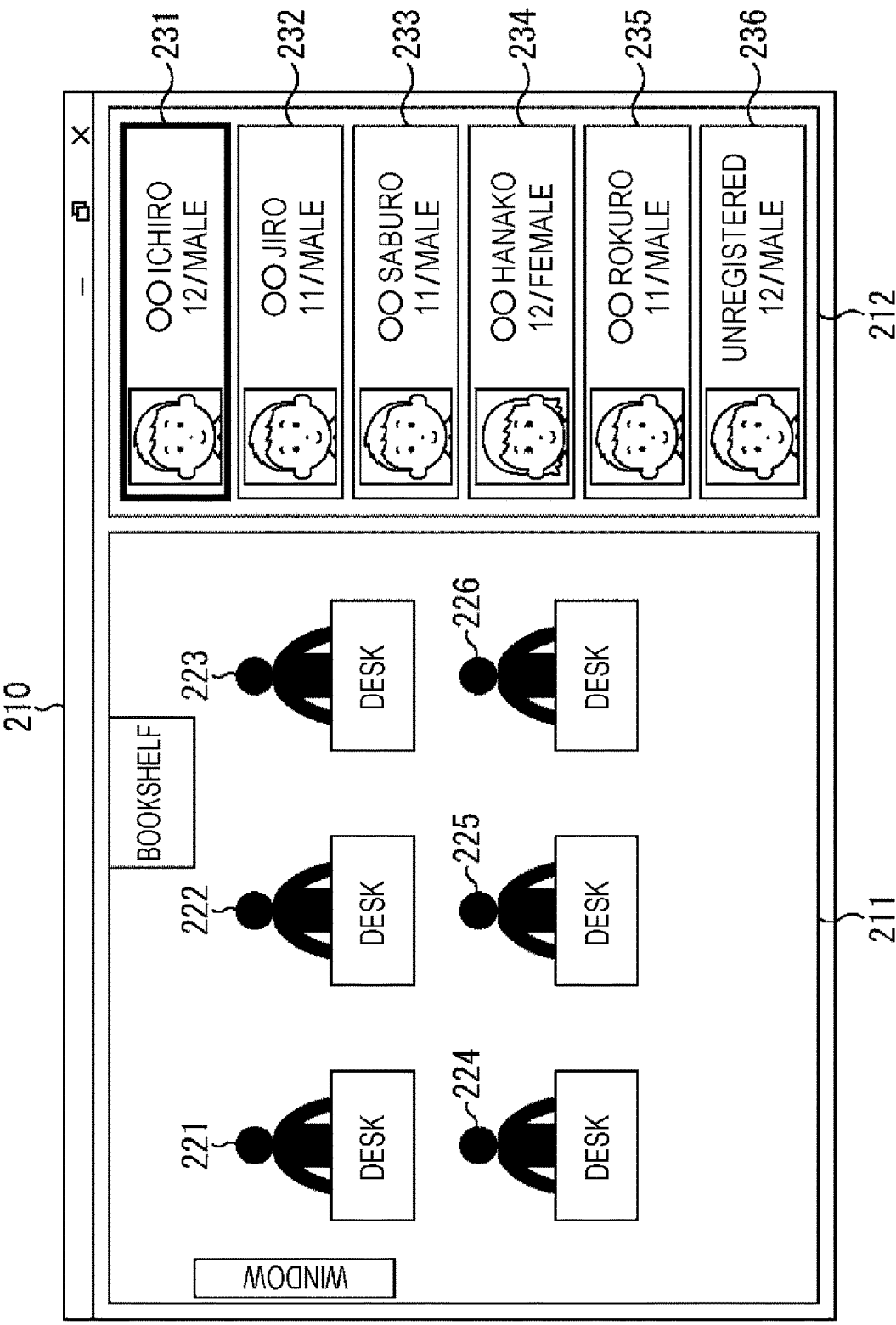
FIG. 16 is a diagram illustrating an example of the parameter table management screen.

FIG. 16 is a diagram illustrating an example of the parameter table management screen.

A lecture room information display area 211 and an auditor information display area 212 are provided on the parameter table management screen 210.

The lecture room information display area 211 is an area in which the lecture room information is displayed. In the example of FIG. 16, the window, the bookshelf, and the desks in the lecture room are displayed in the form illustrated in FIG. 13, and pieces of the position information 221 to 226 corresponding to the auditors U1 to U6, respectively, are displayed.

The auditor information display area 212 is an area in which the auditor information is displayed. In the example of FIG. 16, pieces of the auditor information 231 to 236 corresponding to the auditors U1 to U6, respectively, are displayed.

As described above, the position information and the auditor information included in the lecture room information are associated with each other. For example, in the auditor information display area 212, if the auditor information 231 corresponding to the auditor U1 is clicked, in the lecture room information display area 211, the position information 221 corresponding to the auditor U1 is emphatically displayed or the like.

In addition, as described above, since the auditor U4 is newly registered (added) in the parameter table, the auditor information 236 corresponding to the auditor U4 is set to "not registered" and is displayed in a color different from, for example, other auditor information 231 to 235.

The age/gender information of the auditor U4 added to the parameter table is displayed in the auditor information 236, but the age/gender information estimated by the age/gender estimation unit 74 is not necessarily correct.

Figure 17:
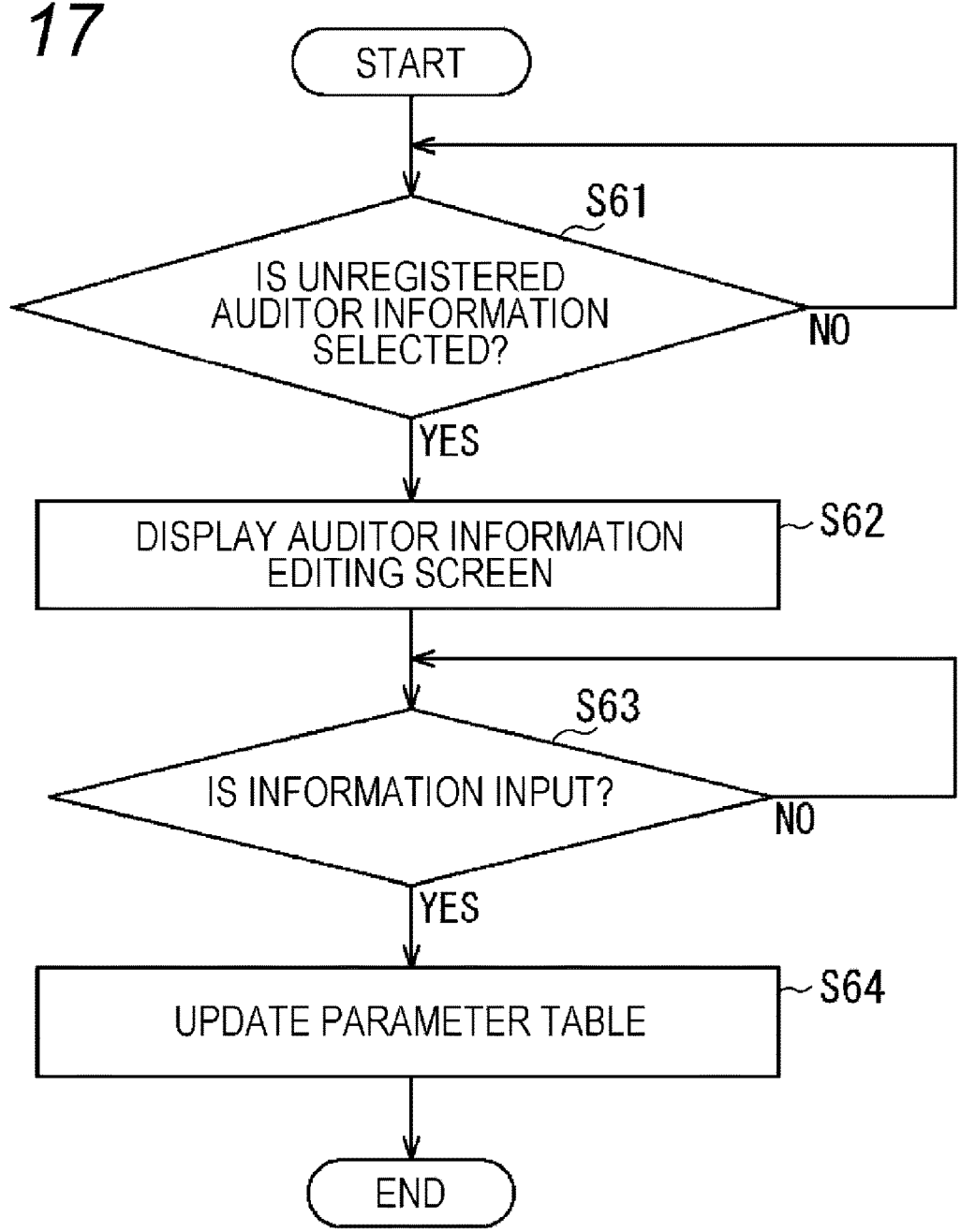
FIG. 17 is a flowchart illustrating a correction process of auditor information.

Therefore, a process of correcting the information registered in the parameter table will be described with reference to the flowchart of FIG. 17.

In step S61, the parameter setting unit 76 determines whether or not unregistered auditor information has been selected on the basis of the information from the input/output apparatus 30.

While the unregistered auditor information is not selected, step S61 is repeated, and if the unregistered auditor information is selected, the process proceeds to step S62.

In step S62, the display control unit 79 displays the auditor information editing screen. The auditor information editing screen is a UI that receives change and input of the auditor information.

In step S63, the parameter setting unit 76 determines whether or not information has been input to the auditor information editing screen on the basis of the information from the input/output apparatus 30.

While information is not input to the auditor information editing screen, step S63 is repeated. If information is input to the auditor information editing screen, the process proceeds to step S64.

In step S64, the parameter setting unit 76 updates the information of the corresponding auditor in the parameter table by using the information input to the auditor information editing screen.

Figure 18:
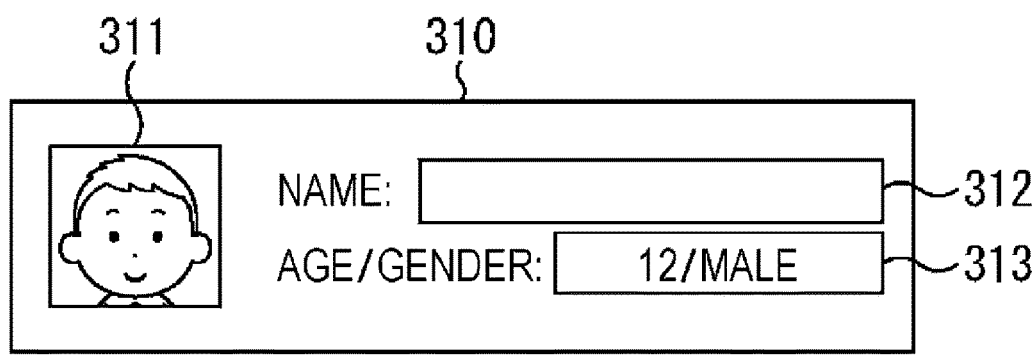
FIG. 18 is a diagram illustrating an example of an auditor information editing screen.

For example, if unregistered auditor information 236 is selected on the parameter table management screen in FIG. 16 by, for example, double click or the like, an auditor information editing screen 310 as illustrated in FIG. 18 is displayed.

In addition to face information 311, a name information input field 312 and an age/gender information input field 313 are displayed on the auditor information editing screen 310. In the example of FIG. 18, the face image is displayed as the face information 311, and age/gender information estimated by age/gender estimation unit 74 is displayed in the age/gender information input field 313.

The user changes the auditor information into correct information by inputting the name information in the name information input field 312 or reentering the age/gender information in the age/gender information input field 313.

The auditor information newly input in this manner is used for detecting such a type of behavior for which the behavior detection parameter has not yet been optimized, for example.

With respect to a lecture room where a lecture using the lecture capturing system has never been performed, the position information of the auditor is not displayed in the lecture room information display area 211, nor is it associated with the auditor information.

Therefore, the process of associating the position information of the auditor with the auditor information in the lecture room information will be described with reference to the flowchart of FIG. 19.

In step S71, the parameter setting unit 76 determines whether or not a predetermined position is designated in the lecture room information displayed in the lecture room information display area 211 on the basis of the information from the input/output apparatus 30.

While a predetermined position is not designated in the lecture room information, step S71 is repeated, and if a predetermined position is designated in the lecture room information, the process proceeds to step S72.

In step S72, the parameter setting unit 76 adds position information to the position designated in the lecture room information. At this point, the added position information is not position information of any auditor.

In step S73, on the basis of the information from the input/output apparatus 30, the parameter setting unit 76 determines whether or not the auditor information corresponding to the added position information is designated.

While the auditor information corresponding to the added position information is not designated, step S73 is repeated, and if the auditor information corresponding to the added position information is designated, the process proceeds to step S74.

In step S74, the parameter setting unit 76 associates the added position information with the designated auditor information.

Figure 20:
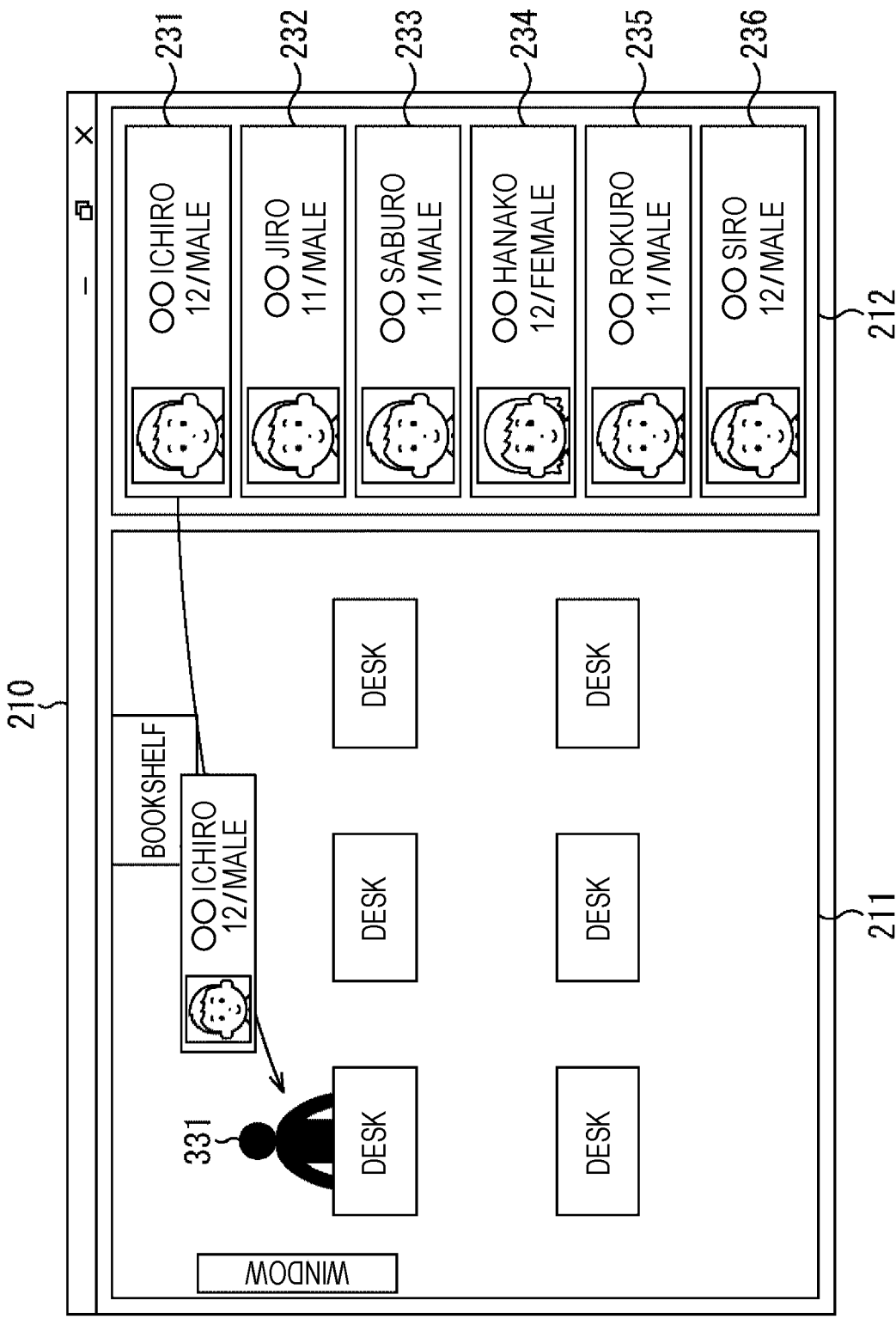
FIG. 20 is a diagram illustrating association of position information with auditor information.

FIG. 20 is a diagram illustrating an example of a parameter table management screen on which lecture room information of a lecture room where a lecture using a lecture capturing system has never been performed is displayed.

For example, in the lecture room information display area 211 of the parameter table management screen in FIG. 20, if the position in the vicinity of the desk at the upper left is designated by, for example, clicking or the like, position information 331 is added. After that, if the auditor information 231 is designated from the auditor information display area 212 to the position information 331 by, for example, the drag and drop or the like, the position information 331 and the auditor information 231 are associated with each other.

The information associated in this manner is used for giving a lecture newly using the lecture capturing system in the lecture room, for example.

Since there is no information of the auditors who have never listened to a lecture using the lecture capturing system in the parameter table, auditor information is not displayed in the auditor information display area 212.

Figure 21:
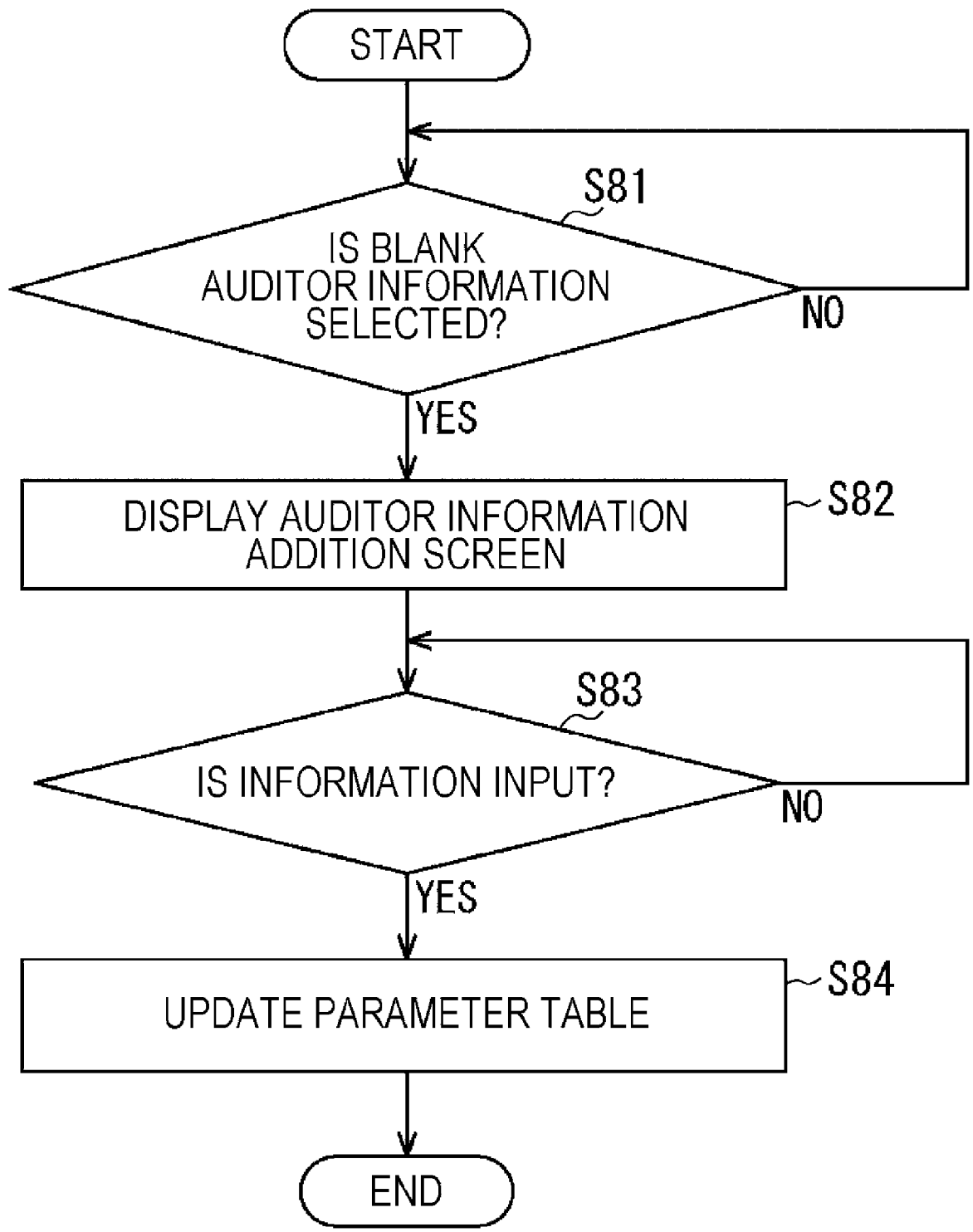
FIG. 21 is a flowchart illustrating an auditor information adding process.

Therefore, a process of adding auditor information in advance with respect to an auditor having no auditor information in the parameter table will be described with reference to the flowchart of FIG. 21.

In step S81, the parameter setting unit 76 determines whether or not the blank auditor information has been selected on the basis of the information from the input/output apparatus 30.

Figure 22:
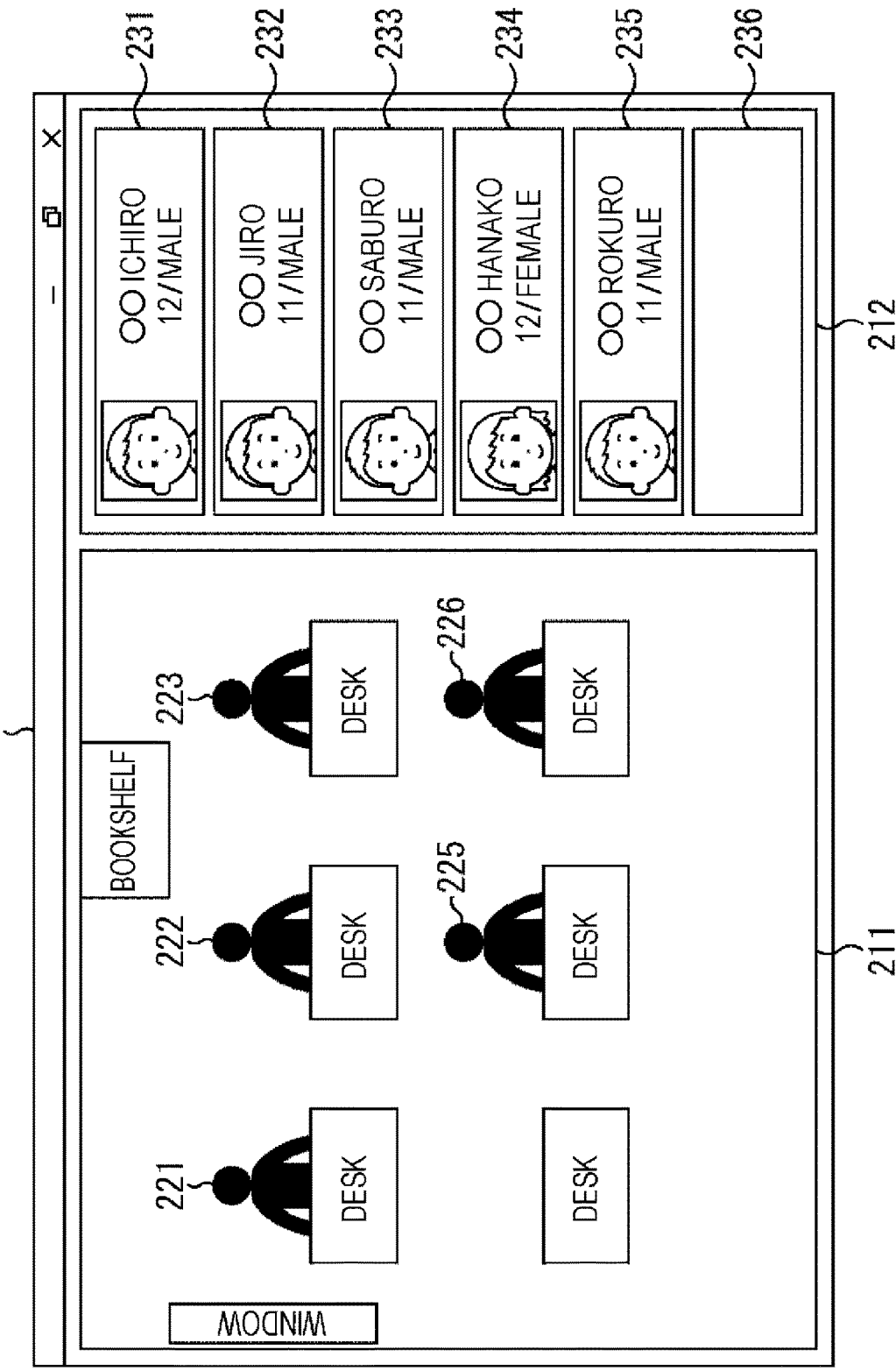
FIG. 22 is a diagram illustrating addition of auditor information.

FIG. 22 is a diagram illustrating an example of a parameter table management screen including blank auditor information. In FIG. 22, auditor information 236 is the blank auditor information.

While the blank auditor information is not selected, step S81 is repeated, and if the blank auditor information 236 is selected by double clicking or the like, for example, the process proceeds to step S82.

In step S82, the display control unit 79 displays an auditor information addition screen. The auditor information addition screen is a UI in which all of the face information 311, the name information input field 312, and the age/gender information input field 313 are blank in a similar layout to the auditor editing screen in FIG. 18.

In step S83, on the basis of the information from the input/output apparatus 30, the parameter setting unit 76 determines whether or not information is input to the auditor information addition screen.

While information is not input to the auditor information addition screen, step S83 is repeated, and if information is input to the auditor information addition screen, the process proceeds to step S84.

In step S84, the parameter setting unit 76 updates the parameter table by using the information input to the auditor information addition screen. The auditor information of the auditor is added to the updated parameter table.

Figure 19:
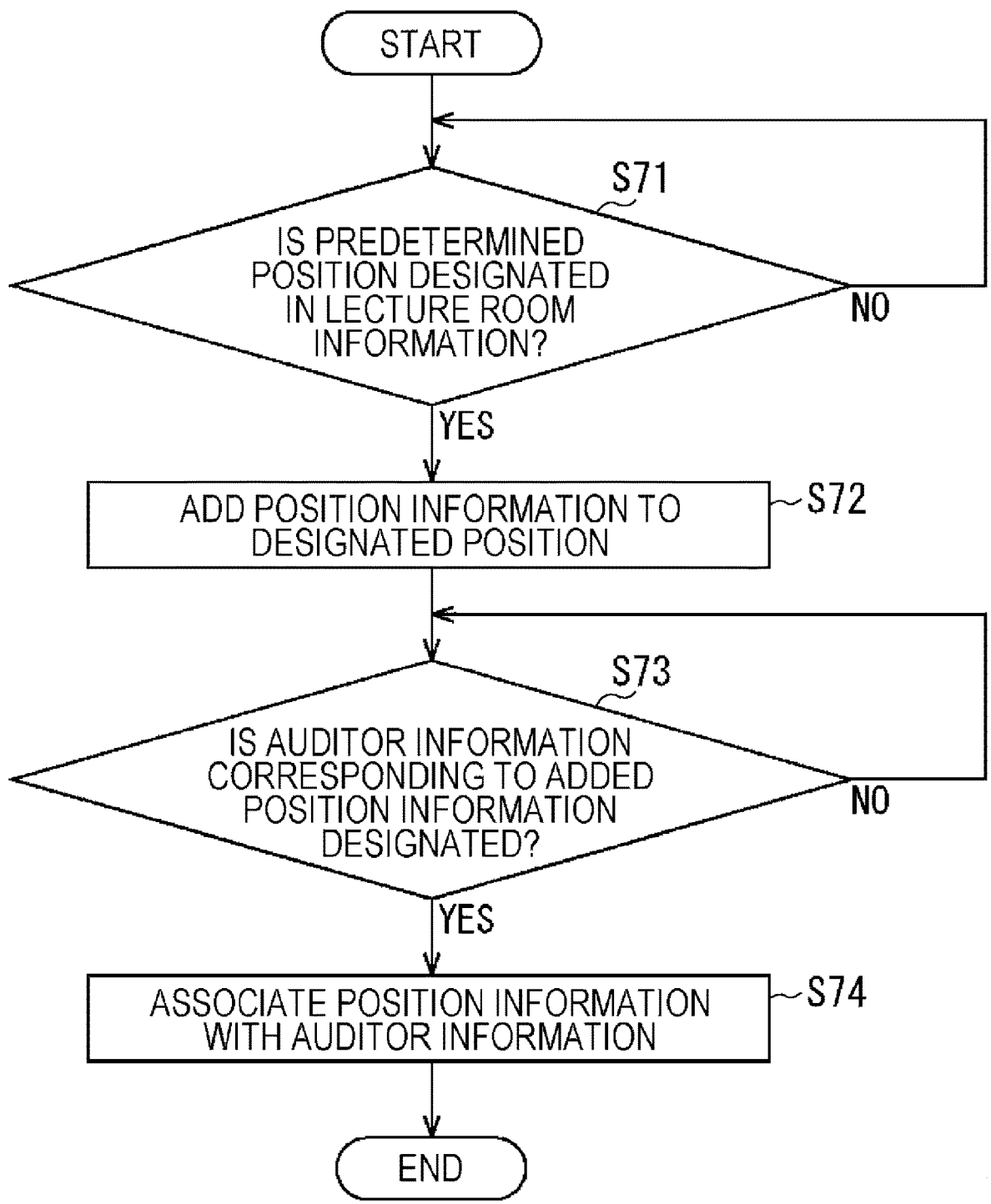
FIG. 19 is a flowchart illustrating a process of associating position information with auditor information.

The added auditor information can be associated with the position information of the auditor in the lecture room information by a similar procedure as in FIG. 19.

The information correlated in this manner is used when an added auditor listens to a lecture newly using a lecture capturing system, and the like.

According to the above processes, it may be possible to easily change or add the information of the auditor in the parameter table, so that the auditor can be easily managed and, eventually, the operations of the system can be simplified.

6. Modified Example

Hereinafter, modified examples of the above-described embodiment will be described.

(With Respect to Age/Gender Estimation)

Age/gender estimation may be performed on the basis of not only the face information but also the skeleton, shape, and motion of the body based on the posture information.

In addition, in a case where the age/gender information has already been registered as auditor information of the parameter table, the age/gender estimation may not be performed, and the registered age/gender information may be used.

(Person Identification)

Calculation of a personal characteristic quantity for identifying a person may be performed on the basis of not only the face information but also the skeleton and body shape based on the posture information and its motion.

(Calculation of Behavior Detection Parameter)

The calculation of behavior detection parameters is not limited to both age and gender, and may be performed on the basis of either one.

In addition, the calculation of the behavior detection parameter may be performed on the basis of not only age and gender but also information indicating race or the like.

Furthermore, the calculation of the behavior detection parameter may be performed by using the information associated with physical characteristics such as height, weight, and sitting height. In this case, in addition to the name information and the age/gender information, the information associated with the physical characteristics such as height, weight, and sitting height is allowed to be input in the auditor information editing screen (auditor information addition screen).

(Others)

Generally, in many cases, the ages of the auditors in one lecture are often close. Therefore, for the auditors who have never listened to a lecture using the lecture capturing system, the ages of age/gender information of all auditors may be collectively input in the procedure of FIG. 21.

In a case where the position of the auditor in the lecture room is associated with the auditor information, the behavior detection parameter may be determined from the auditor information corresponding to the position of the auditor obtained from the posture information obtained by the posture detection without performing the person identification.

In addition, in a case where the information of the timetable is obtained as the object information, the ages of all the auditors who are targets of the behavior detection may be automatically set collectively from the subjects and the like in the timetable. The information of the timetable may be detected from the timetable displayed in the lecture room, or the information of the timetable may be stored in the recording apparatus 40 and may be read out. In addition, the information of the timetable may be acquired from an external apparatus via a network.

Furthermore, in a case where the information of the timetable and the information of the seat table are obtained as the object information, the positions of the auditors in the lecture room and the auditor information may be automatically associated with each lecture.

The above description is made under the assumption that the target of the behavior detection is a person, but the target of the behavior detection may be an animal such as a dog or a cat.

7. Configuration Example of Computer

The series of processes described above may be executed by hardware or software. In a case where a series of processes is executed by software, a program constituting the software is installed from a program recording medium into a computer incorporated into dedicated hardware, a general purpose personal computer, or the like.

Figure 23:
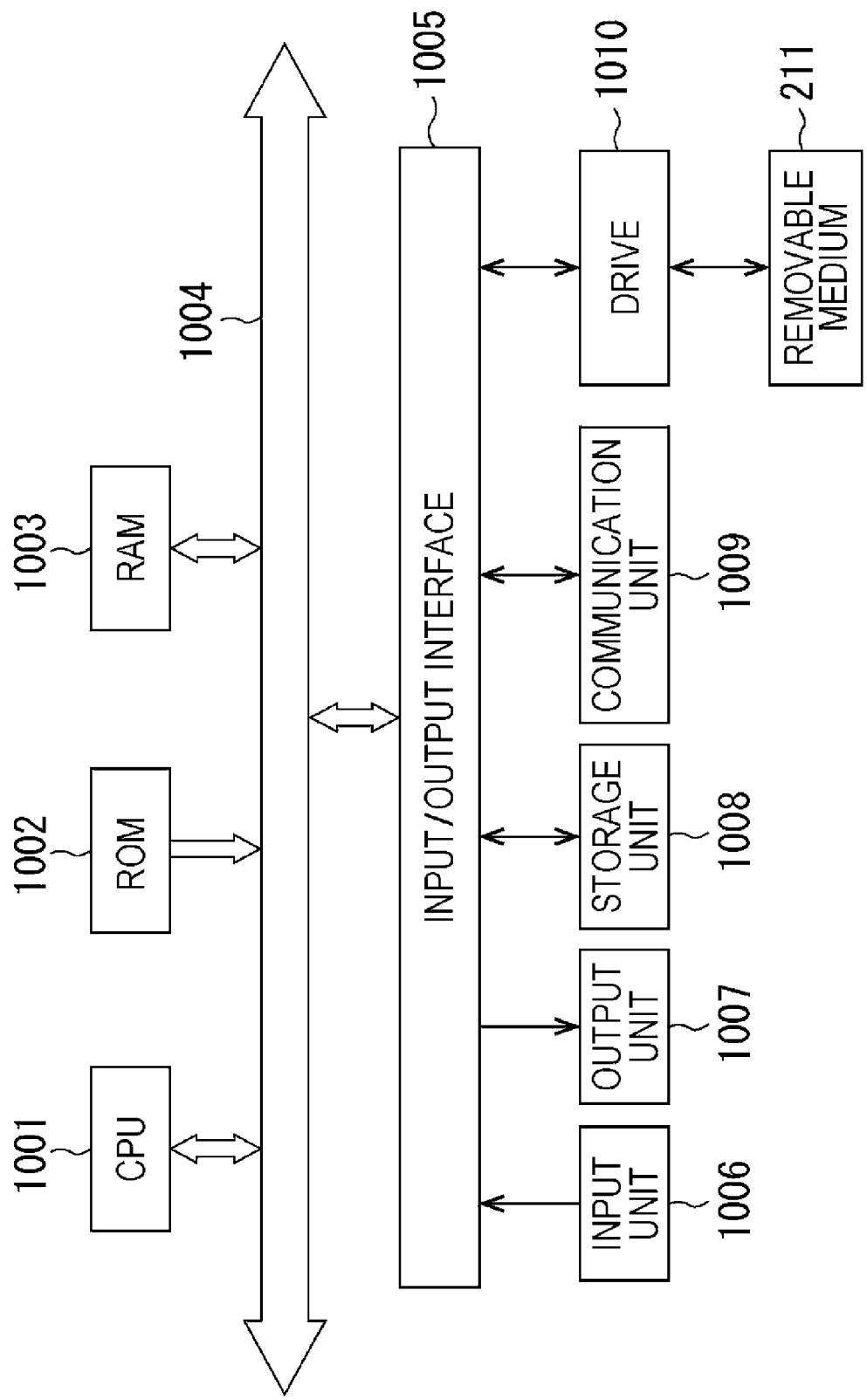
FIG. 23 is a block diagram illustrating a configuration example of a computer.

FIG. 23 is a block diagram illustrating an example of a hardware configuration of a computer that executes the above-described series of processes by a program.

The information processing apparatus 20 described above is realized by a computer having the configuration illustrated in FIG. 23.

The CPU 1001, the ROM 1002, and the RAM 1003 are connected to each other via a bus 1004.

An input/output interface 1005 is further connected to the bus 1004. An input unit 1006 including a keyboard, a mouse, or the like, and an output unit 1007 including a display, a speaker, and the like are connected to the input/output interface 1005. In addition, a drive 1010 for driving a storage unit 1008 including a hard disk, a nonvolatile memory, or the like, a communication unit 1009 including a network interface, or the like, and a removable medium 1011 is connected to the input/output interface 1005.

In the computer configured as described above, for example, the CPU 1001 performs a series of processes described above by loading a program stored in the storage unit 1008 to the RAM 1003 via the input/output interface 1005 and the bus 1004 and executing the program.

The program executed by the CPU 1001 is recorded on, for example, the removable medium 1011 or provided via a wired or wireless transmission medium such as a local area network, the Internet, or a digital broadcast and installed in the storage unit 1008.

In addition, the program executed by the computer may be a program in which processes are performed in time series in accordance with the order described in this specification or may be a program on which processes are performed in parallel or at a necessary timing such as when a call is made.

8. Application Example (Application Example to Mobile Body Control System)

The technology according to the present disclosure can be applied to various products. For example, the technology according to the present disclosure may be realized as an apparatus mounted on any one of types of mobile bodies such as an automobile, an electric vehicle, a hybrid electric vehicle, a motorcycle, a bicycle, a personal mobility, an airplane, a drone, a ship, a robot, a construction machine, and an agricultural machine (tractor).

Figure 24:
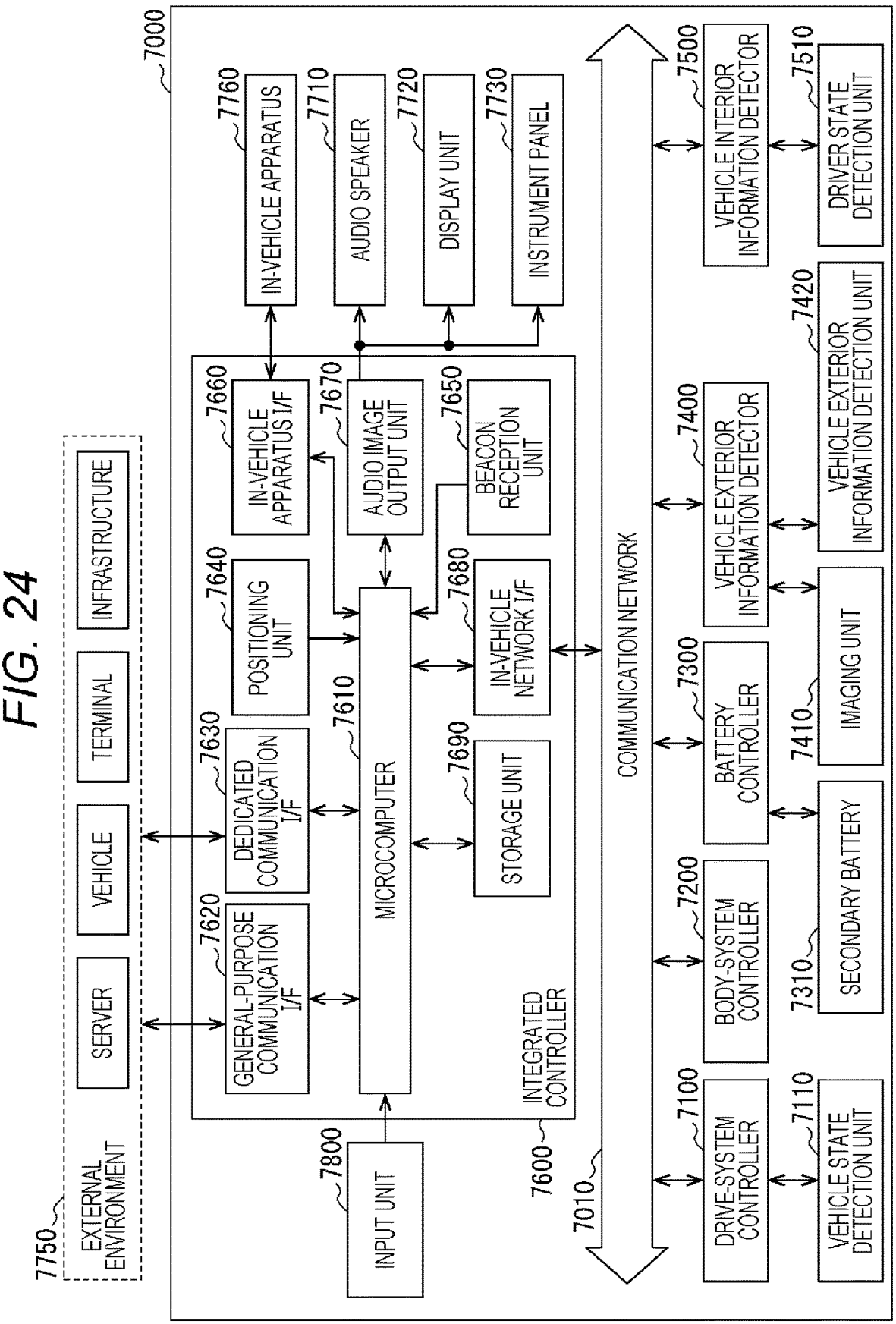
FIG. 24 is a block diagram illustrating an example of a schematic configuration of a vehicle control system.

FIG. 24 is a block diagram illustrating a schematic configuration example of a vehicle control system 7000 which is an example of a mobile body control system to which the technology according to the present disclosure can be applied. The vehicle control system 7000 includes a plurality of electronic controllers connected via a communication network 7010. In the example illustrated in FIG. 24, the vehicle control system 7000 includes a drive-system controller 7100, a body-system controller 7200, a battery controller 7300, a vehicle exterior information detector 7400, a vehicle interior information detector 7500, and an integrated controller 7600. The communication network 7010 connecting a plurality of the control units may be an in-vehicle communication network in accordance with an arbitrary standard such as Controller Area Network (CAN), Local Interconnect Network (LIN), Local Area Network (LAN), or FlexRay (registered trademark).

Each of the controllers includes a microcomputer which performs calculation processes according to various programs, a storage unit which stores the programs executed by the microcomputer, parameters used for various calculations, or the like, and a drive circuit which drives various apparatuses as control targets. Each of the controllers includes a network I/F for communicating with another controller via the communication network 7010 and a communication I/F for performing communication by wired communication or wireless communication with apparatuses inside or outside the vehicle, sensors, or the like. In FIG. 24, as the functional configurations of the integrated controller 7600, a microcomputer 7610, a general-purpose communication I/F 7620, a dedicated communication I/F 7630, a positioning unit 7640, a beacon reception unit 7650, an in-vehicle apparatus I/F 7660, an audio image output unit 7670, an in-vehicle network I/F 7680, and a storage unit 7690 are illustrated. Similarly, the other controllers include a microcomputer, a communication I/F, a storage unit, and the like.

The drive-system controller 7100 controls the operations of the apparatuses related to the drive system of the vehicle according to various programs. For example, the drive-system controller 7100 functions as a control device of a driving force generating apparatus for generating a driving force of a vehicle such as an internal combustion engine or a driving motor, a driving force transmitting mechanism for transmitting a driving force to wheels, a steering mechanism for adjusting a rudder angle of a vehicle, a braking apparatus for generating a braking force of a vehicle, and the like. The drive-system controller 7100 may have a function as a control device such as Antilock Brake System (ABS) or Electronic Stability Control (ESC).

A vehicle state detection unit 7110 is connected to the drive-system controller 7100. The vehicle state detection unit 7110 includes at least one of for example, a gyro sensor for detecting an angular velocity of a rotational motion of a body of a vehicle, an acceleration sensor for detecting acceleration of a vehicle, or a sensor for detecting an operation amount of an accelerator pedal, an operation amount of a brake pedal, a steering angle of a steering wheel, an RPM of an engine, a rotation speed of a wheel, or the like. The drive-system controller 7100 performs calculation processes by using signals input from the vehicle state detection unit 7110 and controls an internal combustion engine, a drive motor, a power steering device, a brake device, and the like.

The body-system controller 7200 controls operations of various devices equipped on the vehicle body according to various programs. For example, the body-system controller 7200 functions as a keyless entry system, a smart key system, a power window device, or a control device for various lamps such as head lamps, back lamps, brake lamps, turn indicator lamps, or fog lamps. In this case, the body-system controller 7200 can receive radio waves transmitted from a portable apparatus that substitutes keys or signals of various switches. The body-system controller 7200 receives input of these radio waves or signals and controls the door lock device, the power window device, the lamp, and the like of the vehicle.

The battery controller 7300 controls a secondary battery 7310 which is a power supply source of the driving motor according to various programs. For example, information such as a battery temperature, a battery output voltage, or a remaining capacity of a battery from a battery apparatus including the secondary battery 7310 is input to the battery controller 7300. The battery controller 7300 performs a calculation process by using these signals and controls temperature adjustment of the secondary battery 7310 or controls a cooling apparatus or the like provided in the battery apparatus.

The vehicle exterior information detector 7400 detects information outside the vehicle equipped with the vehicle control system 7000. For example, at least one of an imaging unit 7410 or a vehicle exterior information detection unit 7420 is connected to the vehicle exterior information detector 7400. The imaging unit 7410 includes at least one of a Time Of Flight (ToF) camera, a stereoscopic camera, a monocular camera, an infrared camera, or other cameras. The vehicle exterior information detection unit 7420 includes at least one of, for example, an environment sensor for detecting current climate or weather or an ambient information detection sensor for detecting other vehicles, obstacles, pedestrians, or the like around the vehicle on which the vehicle control system 7000 is mounted.

The environment sensor may be, for example, at least one of a raindrop sensor for detecting rainfall, a fog sensor for detecting fog, a sunshine sensor for detecting a degree of sunshine, or a snow sensor for detecting snowfall. The ambient information detection sensor may be at least one of an ultrasonic sensor, a radar device, or a Laser Imaging Detection and Ranging (LIDAR) device. The imaging unit 7410 and the vehicle exterior information detection unit 7420 may be provided as independent sensors or devices, respectively or may be provided as a device in which a plurality of sensors or devices are integrated.

Figure 25:
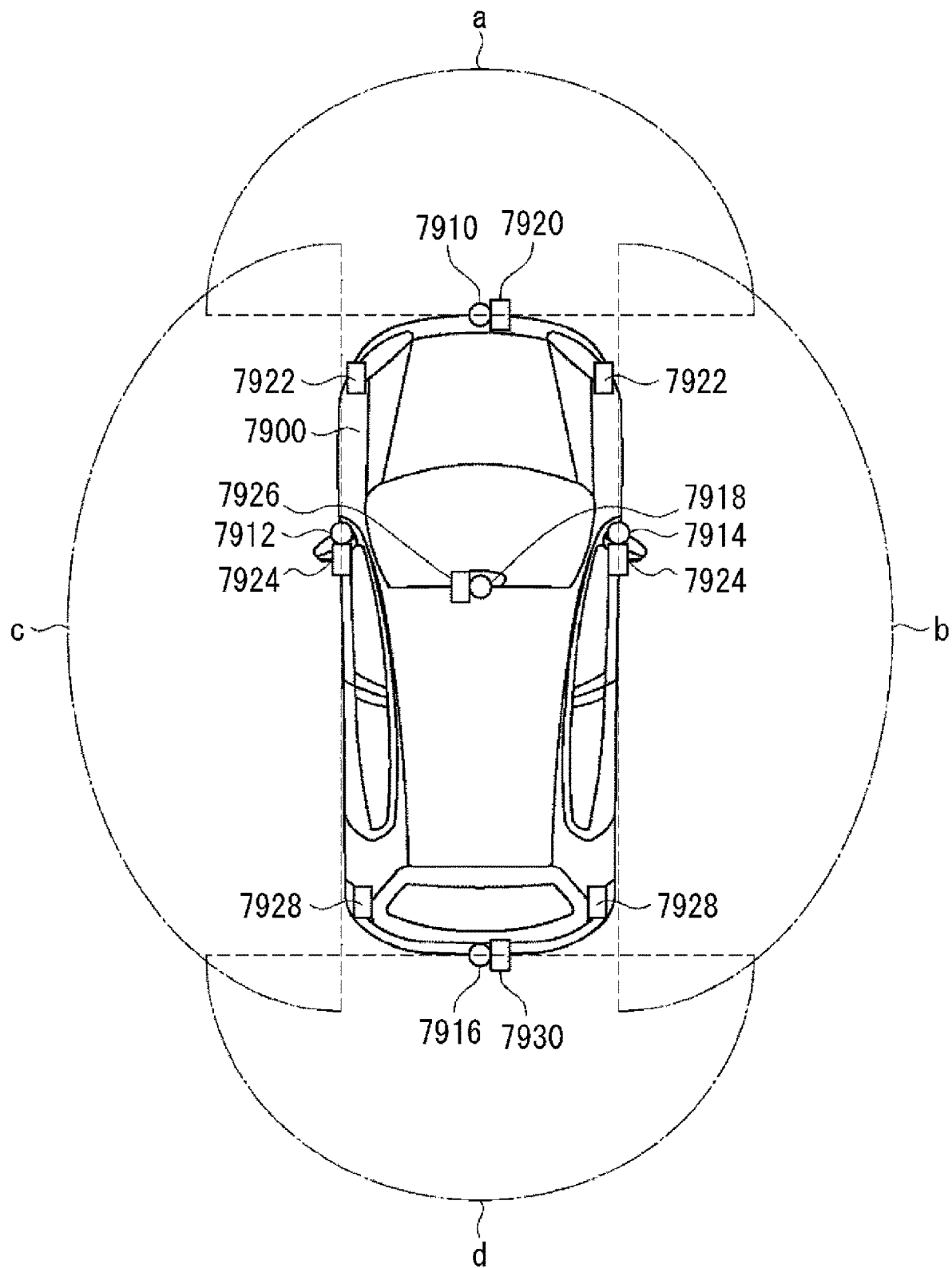
FIG. 25 is an explanatory diagram illustrating an example of installation positions of a vehicle exterior information detection unit and an imaging unit.

Herein, FIG. 25 illustrates an example of installation positions of the imaging unit 7410 and the vehicle exterior information detection unit 7420. The imaging units 7910, 7912, 7914, 7916, and 7918 are provided, for example, at least one of a front nose, side mirrors, a rear bumper, back doors, or an upper portion of the windshield in the occupant compartment of the vehicle 7900. The imaging unit 7910 provided for the front nose and the imaging unit 7918 provided in the upper portion of the windshield in the occupant compartment mainly acquire an image ahead of the vehicle 7900. The imaging units 7912 and 7914 provided in the side mirrors mainly acquire images of the sides of the vehicle 7900. The imaging unit 7916 provided in the rear bumper or the back doors mainly acquires an image behind the vehicle 7900. The imaging unit 7918 provided in the upper portion of the windshield in the occupant compartment is mainly used for detection of preceding vehicles, pedestrians, obstacles, traffic lights, traffic signs, lanes, or the like.

In addition, FIG. 25 illustrates an example of imaging ranges of the imaging units 7910, 7912, 7914, and 7916. The imaging range "a" indicates the imaging range of the imaging unit 7910 provided in the front nose, the imaging ranges "b" and "c" indicate the imaging ranges of the imaging units 7912 and 7914 provided in the side mirrors, and the imaging range "d" indicates the imaging range of the imaging unit 7916 provided in the rear bumper or the back door. For example, by overlapping the image data captured by the imaging units 7910, 7912, 7914, and 7916, an overhead view image of the vehicle 7900 viewed from the above is obtained.

The vehicle exterior information detection units 7920, 7922, 7924, 7926, 7928, and 7930 provided on the front, rear, side, corner, and upper portion of the windshield in the occupant compartment of the vehicle 7900 may be, for example, ultrasonic sensors or radar devices. The vehicle exterior information detection units 7920, 7926, and 7930 provided on the front nose, the rear bumper, the back doors, and upper portion of the windshield in the occupant compartment of the vehicle 7900 may be, for example, LIDAR devices. The vehicle exterior information detection units 7920 to 7930 are mainly used for detecting preceding vehicles, pedestrians, obstacles, and the like.

Returning to FIG. 24, the description will be continued. The vehicle exterior information detector 7400 causes the imaging unit 7410 to capture an image of the exterior of the vehicle and receives the captured image data. In addition, the vehicle exterior information detector 7400 receives the detection information from the connected vehicle exterior information detection unit 7420. In a case where the vehicle exterior information detection unit 7420 is an ultrasonic sensor, a radar device, or a LIDAR device, the vehicle exterior information detector 7400 transmits ultrasonic waves, electromagnetic waves, or the like and receives information of the received reflected waves. The vehicle exterior information detector 7400 may perform an object detection process or a distance detection process of persons, cars, obstacles, signs, characters on a road surface, and the like on the basis of the received information. The vehicle exterior information detector 7400 may perform an environment recognition process for recognizing rainfall, fog, a road surface condition, and the like on the basis of the received information. The vehicle exterior information detector 7400 may calculate the distance to the object outside the vehicle on the basis of the received information.

In addition, the vehicle exterior information detector 7400 may perform an image recognition process or a distance detection process for recognizing people, cars, obstacles, signs, characters on a road surface, and the like on the basis of the received image data. The vehicle exterior information detector 7400 may perform a process such as distortion correction or position alignment on the received image data and generate an overhead view image or a panorama image by combining the image data captured by different imaging units 7410. The vehicle exterior information detector 7400 may perform a viewpoint conversion process by using an image data captured by other imaging units 7410.

The vehicle interior information detector 7500 detects information inside the vehicle. A driver state detection unit 7510 that detects, for example, the state of the driver is connected to the vehicle interior information detector 7500. The driver state detection unit 7510 may include a camera that images the driver, a biometric sensor that detects biological information of the driver, a microphone that collects sounds in the interior of the vehicle, and the like. The biometric sensor is provided, for example, to a seat surface, a steering wheel, or the like and detects biometric information of the occupant taking a seat or a driver holding the steering wheel. The vehicle interior information detector 7500 may calculate a degree of fatigue or a degree of concentration of the driver on the basis of the detection information input from the driver state detection unit 7510 or may determine whether or not the driver is dozing off. The vehicle interior information detector 7500 may perform a noise canceling process or the like on the collected sound signal.

The integrated controller 7600 controls the overall operations in the vehicle control system 7000 in accordance with various programs. An input unit 7800 is connected to the integrated controller 7600. The input unit 7800 is realized by a device such as a touch panel, a button, a microphone, a switch, or a lever, which can be input-operated by an occupant, for example. A data obtained by speech-recognizing speech input by a microphone may be input to the integrated controller 7600. The input unit 7800 may be, for example, a remote control device using infrared rays or other radio waves or may be an external connection apparatus such as a mobile phone or a Personal Digital Assistant (PDA) corresponding to the operations of the vehicle control system 7000. The input unit 7800 may be, for example, a camera, and in this case, an occupant can input information by gesture. Alternatively, a data obtained by detecting a motion of a wearable apparatus worn by the occupant may be input. In addition, the input unit 7800 may include, for example, an input control circuit or the like that generates an input signal on the basis of information input by an occupant or the like using the above-described input unit 7800 and outputs the input signal to the integrated controller 7600. By operating the input unit 7800, the occupant or the like inputs various data to the vehicle control system 7000 or instructs the vehicle control system 7000 to perform a processing operation.

The storage unit 7690 may include a Read Only Memory (ROM) that stores various programs to be executed by the microcomputer and a Random Access Memory (RAM) that stores various parameters, calculation results, sensor values, or the like. In addition, the storage unit 7690 may be realized by a magnetic storage device such as a Hard Disc Drive (HDD), a semiconductor storage device, an optical storage device, a magneto-optical storage device, or the like.

The general-purpose communication I/F 7620 is a general-purpose communication I/F that relays communication with various apparatuses existing in an external environment 7750. The general-purpose communication I/F 7620 may be implemented with cellular communication protocols such as GSM (registered trademark) (Global System of Mobile communications), WiMAX (registered trademark), Long Term Evolution (LTE) (registered trademark), and LTE-Advanced (LTE-A) or other wireless communication protocols such as wireless LAN (also referred to as Wi-Fi (registered trademark)) and Bluetooth (registered trademark). The general-purpose communication I/F 7620 may be connected to an apparatus (for example, an application server or a control server) existing on an external network (for example, the Internet, a cloud network or a company specific network), for example, via a base station or an access point. In addition, the general-purpose communication I/F 7620 may be connected to a terminal existing in the vicinity of the vehicle (for example, a terminal of a driver, a pedestrian, a store, or an Machine Type Communication terminal (MTC) by using, for example, a Peer To Peer (P2P) technology.

The dedicated communication I/F 7630 is a communication I/F supporting a communication protocol formulated for the purpose of use in a vehicle. For example, the dedicated communication I/F 7630 may be implemented with a standard protocol such as Wireless Access in Vehicle Environment (WAVE), Dedicated Short Range Communications (DSRC), or a cellular communication protocol which is a combination of lower layer IEEE 802.11p and upper layer IEEE 1609. Typically, the dedicated communication I/F 7630 performs V2X communication which is a concept including one or more of vehicle-to-vehicle communication, vehicle-to-infrastructure communication, vehicle-to-home communication, and vehicle-to-pedestrian communication.

The positioning unit 7640 generates position information including the latitude, longitude, and altitude of the vehicle by receiving a Global Navigation Satellite System (GNSS) signal from a GNSS satellite (for example, a Global Positioning System (GPS) signal from a GPS satellite) and executes positioning. In addition, the positioning unit 7640 may specify the current position by exchanging signals with the wireless access point or may acquire the position information from a terminal such as a mobile phone, a PHS, or a smartphone having a positioning function.

The beacon reception unit 7650 receives radio waves or electromagnetic waves transmitted from a radio station or the like installed on, for example, a road and acquires information such as a current position, traffic jam, road closing, or a required time. In addition, the functions of the beacon reception unit 7650 may be included in the dedicated communication I/F 7630 described above.

The in-vehicle apparatus I/F 7660 is a communication interface that relays connection between the microcomputer 7610 and various in-vehicle apparatuses 7760 existing in the vehicle. The in-vehicle apparatus I/F 7660 may establish wireless connection by using a wireless communication protocol such as wireless LAN, Bluetooth (registered trademark), Near Field Communication (NFC), or Wireless USB (WUSB). In addition, the in-vehicle apparatus I/F 7660 may establish wired connection of a Universal Serial Bus (USB), a High-Definition Multimedia Interface (HDMI) (registered trademark), a Mobile High-definition Link (MHL), or the like via connection terminals (not illustrated) (and cables if necessary). The in-vehicle apparatus 7760 may include at least one of, for example, a mobile apparatus or a wearable apparatus possessed by an occupant or an information apparatus carried in or attached to the vehicle. In addition, the in-vehicle apparatus 7760 may include a navigation apparatus that performs a route search to an arbitrary destination. The in-vehicle apparatus I/F 7660 exchanges control signals or data signals with these in-vehicle apparatuses 7760.

The in-vehicle network I/F 7680 is an interface that relays communication between the microcomputer 7610 and the communication network 7010. The in-vehicle network I/F 7680 exchanges signals and the like in accordance with a predetermined protocol supported by the communication network 7010.

The microcomputer 7610 of the integrated controller 7600 controls the vehicle control system 7000 in accordance with various programs on the basis of the information acquired via at least one of the general-purpose communication I/F 7620, the dedicated communication I/F 7630, the positioning unit 7640, the beacon reception unit 7650, the in-vehicle apparatus I/F 7660, or the in-vehicle network I/F 7680. For example, the microcomputer 7610 may calculate a control target value of the driving force generating apparatus, the steering mechanism, or the braking apparatus on the basis of acquired vehicle interior information and vehicle exterior information and may output a control command to the drive-system controller 7100. For example, the microcomputer 7610 may perform cooperative control for the purpose of realizing the functions of Advanced Driver Assistance System (ADAS) including collision avoidance or impact mitigation of the vehicle, follow-up driving based on an inter-vehicle distance, vehicle speed maintaining driving, vehicle collision warning, vehicle lane deviation warning, and the like. In addition, the microcomputer 7610 may perform cooperative control for the purpose of automatic driving or the like of autonomously driving the vehicle without depending on the operations of the driver by controlling the driving force generating apparatus, the steering mechanism, the braking apparatus, or the like on the basis of the acquired information regarding the surroundings of the vehicle.

The microcomputer 7610 may generate three-dimensional distance information between the vehicle and surrounding structures and objects such as persons on the basis of the information acquired via at least one of the general-purpose communication I/F 7620, the dedicated communication I/F 7630, the positioning unit 7640, the beacon reception unit 7650, the in-vehicle apparatus I/F 7660, or the in-vehicle network I/F 7680 and may create local map information including the surrounding information of the current position of the vehicle. In addition, the microcomputer 7610 may predict a danger such as collision of vehicles, approaching of a pedestrian or the like, or entry into a closed road and may generate a warning signal on the basis of the acquired information. The warning signal may be, for example, a signal for generating a warning sound or for turning on a warning lamp.

The audio image output unit 7670 transmits at least one output signal of the audio output signal or the image output signal to an output apparatus capable of visually or audibly notifying the occupant of the vehicle or the exterior of the vehicle of the information. In the example of FIG. 24, as an output apparatus, an audio speaker 7710, a display unit 7720, and an instrument panel 7730 are exemplarily illustrated. The display unit 7720 may include at least one of, for example, an onboard display or a head-up display. The display unit 7720 may have an Augmented Reality (AR) display function. Besides these apparatuses, the output apparatus may be a headphone, a wearable apparatus such as a spectacular display worn by an occupant, or other apparatuses such as a projector and a lamp. In a case where the output apparatus is a display apparatus, the display apparatus visually displays the results obtained by various processes performed by the microcomputer 7610 or the information received from other controllers in various formats such as text, image, table, and graph. In addition, in a case where the output apparatus is an audio output apparatus, the audio output apparatus audibly outputs an analog signal obtained by converting an audio signal including reproduced audio data, acoustic data, or the like.

In addition, in the example illustrated in FIG. 24, at least two controllers connected via the communication network 7010 may be integrated into one controller. Alternatively, each controller may be configured with a plurality of controllers. In addition, the vehicle control system 7000 may include another controller (not illustrated). In addition, in the above description, some or all of the functions performed by any one of the controllers may be provided to the other controller. In other words, if information is transmitted and received via the communication network 7010, the predetermined calculation processes may be performed by any controller. Similarly, a sensor or apparatus connected to any controller may be connected to another controller, and a plurality of controllers may transmit and receive detection information to each other via the communication network 7010.

A computer program for realizing each function of the information processing apparatus 20 according to the present embodiment can be implemented in any controller or the like. In addition, a computer-readable recording medium in which such a computer program is stored may be provided. The recording medium is, for example, a magnetic disk, an optical disk, a magneto-optical disk, a flash memory, or the like. In addition, the above-described computer program may be delivered via, for example, a network without using a recording medium.

In the vehicle control system 7000 described above, the information processing apparatus 20 according to the present embodiment can be applied to the integrated controller 7600 according to Application Example illustrated in FIG. 24.

For example, the integrated controller 7600 estimates the age and location of a person from the image data captured by the imaging units 7910, 7912, 7914, and 7916 and sets a behavior detection parameter used for human motion prediction as a threshold used for accident prediction by using the estimation result as input information.

Specifically, in a case where it is estimated that the person detected in the image data is a child of, for example, three to twelve years of age, there is a high possibility that the person is suddenly popping out on the road as compared with an adult. Therefore, in a case where the person detected from the image data is a child, a threshold (behavior detection parameter) for determining "popping out" is set lower than that in the case of an adult. As a result, in a case where it is determined that the child is to be "popping out", the integrated controller 7600 notifies the driver that the possibility that the child is popping out is high or performs control to lower the vehicle speed.

In addition, the integrated controller 7600 may acquire location information such as whether the location estimated on the basis of the image data is a road or a parking lot and may set a threshold value (behavior detection parameter) by further using the acquired location information.

For example, in a case where the location is a parking lot, the vehicle speed does not become high, so that there is no need to set the threshold for determining "popping out" low. On the other hand, in a case where the location is a road, the vehicle speed becomes high, and the possibility that the person is to be popping out is higher than that of the parking lot, so that the threshold for determining "popping out" is set low.

In this manner, since the behavior detection parameters used for human motion prediction are set by applying the information processing apparatus 20 according to the present embodiment to the integrated controller 7600 according to Application Example illustrated in FIG. 24, it may be possible to improve the accuracy of accident prediction.

(Application Example to Endoscopic Surgical System)

The technology (the present technology) according to the present disclosure may be applied to an endoscopic surgery system.

Figure 26:
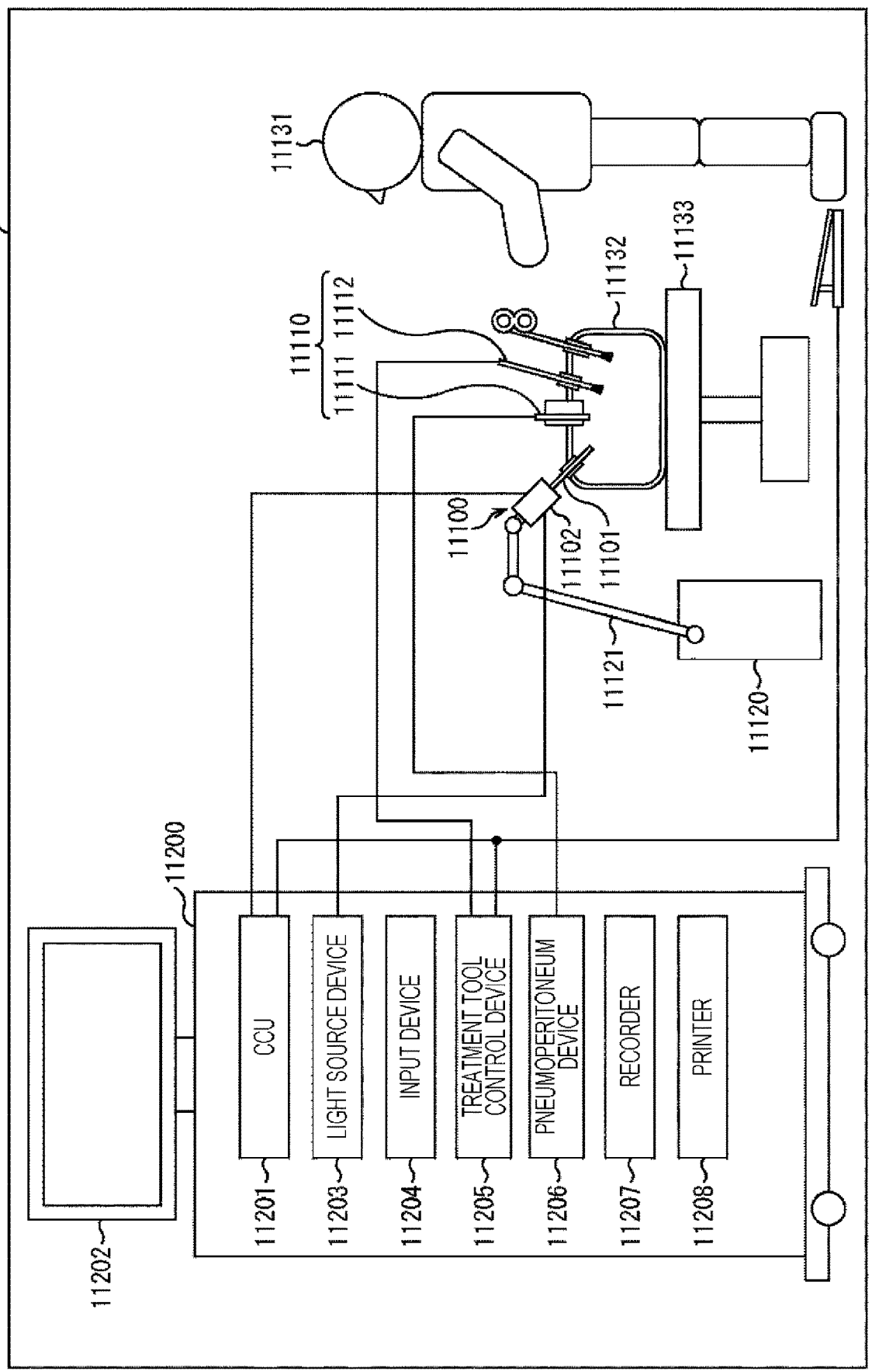
FIG. 26 is a diagram illustrating an example of a schematic configuration of an endoscopic surgery system.

FIG. 26 is a diagram illustrating an example of a schematic configuration of an endoscopic surgery system to which the technology (the present technology) according to the present disclosure can be applied.

In FIG. 26, a surgical operator (doctor) 11131 is performing surgery on a patient 11132 on a patient bed 11133 by using an endoscopic surgery system 11000. As illustrated, the endoscopic surgery system 11000 includes an endoscope 11100, other surgical tools 11110 such as a pneumoperitoneum tube 11111 and an energy treatment tool 11112, a support arm device 11120 for supporting the endoscope 11100, and a cart 11200 on which various devices for endoscopic surgery are mounted.

The endoscope 11100 is configured with a lens barrel 11101 in which a region of a predetermined length from the distal end is inserted into the body cavity of the patient 11132 and a camera head 11102 connected to the proximal end of the lens barrel 11101. In the illustrated example, the endoscope 11100 configured as a so-called rigid mirror having a rigid lens barrel 11101 is illustrated, but the endoscope 11100 may be configured as a so-called soft mirror having a soft lens barrel.

An opening into which the objective lens is fitted is provided at the distal end of the lens barrel 11101. A light source device 11203 is connected to the endoscope 11100, and thus, light generated by the light source device 11203 is guided to the distal end of the lens barrel by a light guide extending to an interior of the lens barrel 11101 and is emitted toward an observation target in the body cavity of the patient 11132 via the objective lens. In addition, the endoscope 11100 may be a direct view mirror or may be a perspective mirror or a side view mirror.

An optical system and an imaging element are provided inside the camera head 11102, and reflected light (observation light) from the observation target is collected on the imaging element by the optical system. The observation light is photoelectrically converted by the imaging element, so that an electric signal corresponding to the observation light, that is, an image signal corresponding to the observation image is generated. The image signal is transmitted as RAW data to a camera controller (CCU: Camera Control Unit) 11201.

The CCU 11201 is configured with a Central Processing Unit (CPU), a Graphics Processing Unit (GPU), or the like and integrally controls the operations of the endoscope 11100 and the display apparatus 11202. In addition, the CCU 11201 receives an image signal from the camera head 11102 and performs various image processes for displaying the image based on the image signal such as a development process (demosaic process), for example, on the image signal.

The display apparatus 11202 displays an image based on the image signal subjected to an image process by the CCU 11201 under the control of the CCU 11201.

The light source device 11203 is configured with a light source such as a light emitting diode (LED), for example, and supplies irradiation light for imaging a site of surgical operation or the like to the endoscope 11100.

An input device 11204 is an input interface to the endoscopic surgery system 11000. The user can input various types of information and input instructions to the endoscopic surgery system 11000 via the input device 11204. For example, the user inputs an instruction to change imaging conditions (type of irradiation light, magnification, focal length, and the like) by the endoscope 11100, or the like.

A treatment tool control device 11205 controls the driving of the energy treatment tool 11112 for cauterizing tissue, cutting incisions, sealing blood vessels, or the like. A pneumoperitoneum device 11206 injects a gas into the body cavity through the pneumoperitoneum tube 11111 so as to inflate the body cavity of the patient 11132 for the purpose of securing the visual field by the endoscope 11100 and securing the working space of the surgical operator. A recorder 11207 is an apparatus capable of recording various types of information associated with surgery. A printer 11208 is an apparatus capable of printing various types of information associated with surgery in various forms such as text, image, and graph.

In addition, the light source device 11203 for supplying irradiation light for imaging a site of surgical operation to the endoscope 11100 can be configured with, for example, a white light source configured with an LED, a laser light source, or a combination thereof. In a case where the white light source is configured with a combination of the RGB laser light sources, since the output intensity and the output timing of each color (each wavelength) can be controlled with high accuracy, the white balance of the captured image can be adjusted by the light source device 11203. In addition, in this case, by irradiating an observation target with the laser light from each of the RGB laser light sources in a time-division manner and controlling the driving of the imaging element of the camera head 11102 in synchronization with the irradiation timing, it may be possible to capture the image corresponding to each of RGB in a time-division manner. According to this method, a color image can be obtained without providing a color filter in the imaging element.

In addition, the driving of the light source device 11203 may be controlled so as to change the intensity of light to be output at predetermined time intervals. By controlling the driving of the imaging element of the camera head 11102 in synchronism with the timing of the change of the intensity of the light, images are acquired in a time-division manner, and by composing the images, an image having a high dynamic range without so-called black-out and white-out can be generated.

In addition, the light source device 11203 may be configured to be capable of supplying light of a predetermined wavelength band corresponding to special light observation. In the special light observation, for example, by using the wavelength dependency of the light absorption in the body tissue, through irradiation with narrow band light compared to the irradiation light (that is, white light) at the time of ordinary observation, so-called narrow band light observation (Narrow Band Imaging) is performed in which a predetermined tissue such as a blood vessel of a mucous membrane surface layer is imaged with high contrast. Alternatively, in the special light observation, fluorescence observation for obtaining an image by fluorescence generated through irradiation with excitation light may be performed. In the fluorescence observation, it may be possible to perform irradiating a body tissue with excitation light to observe the fluorescence from the body tissue (autofluorescence observation), locally injecting a reagent such as indocyanine green (ICG) into the body tissue and irradiating the body tissue with excitation light corresponding to the fluorescence wavelength of the reagent to obtain a fluorescent image, and the like. The light source device 11203 can be configured to be able to supply narrowband light and/or excitation light corresponding to such special light observation.

Figure 27:
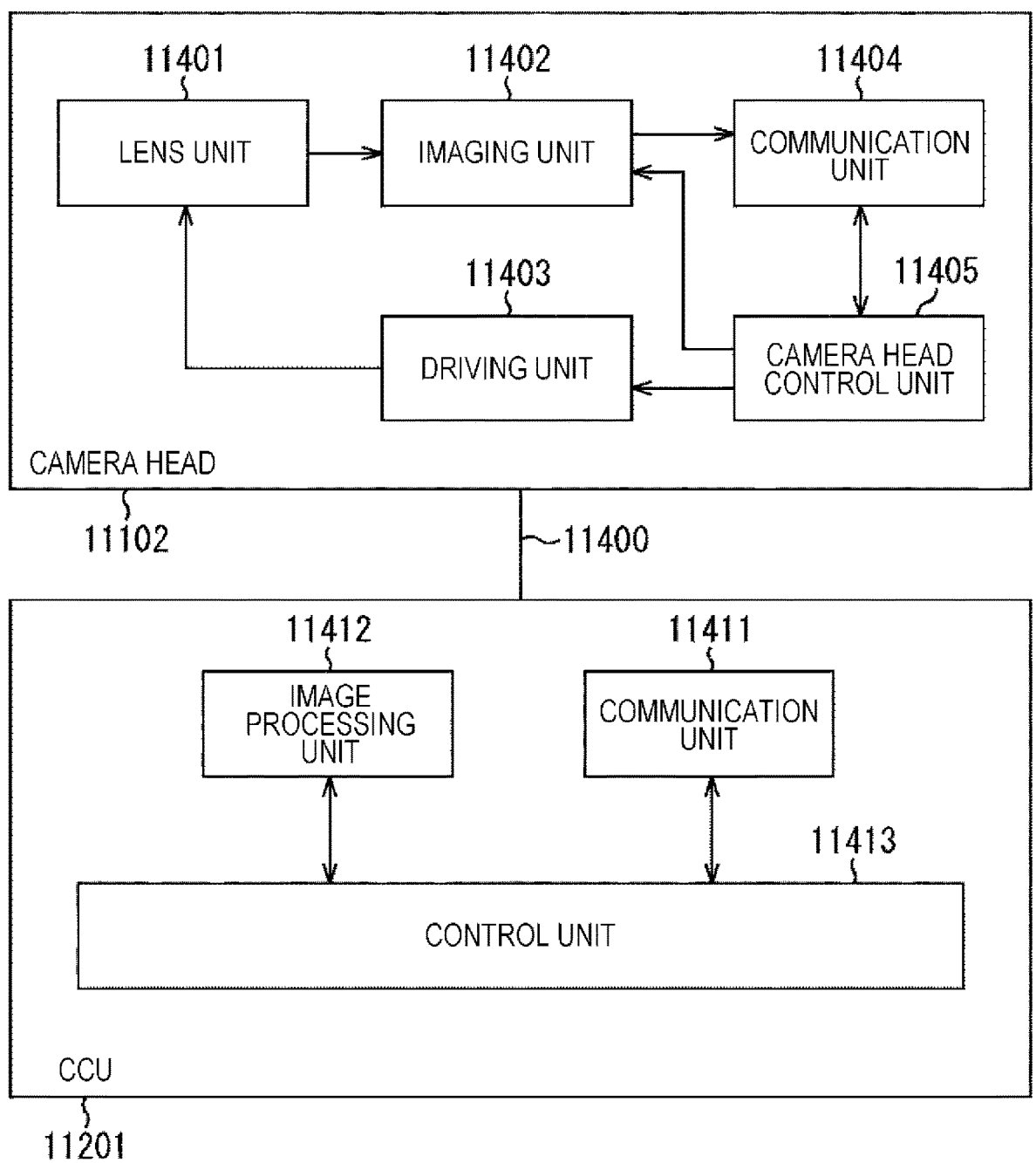
FIG. 27 is a block diagram illustrating an example of a functional configuration of a camera head and a CCU.

FIG. 27 is a block diagram illustrating an example of the functional configuration of the camera head 11102 and the CCU 11201 illustrated in FIG. 26.

The camera head 11102 includes a lens unit 11401, an imaging unit 11402, a driving unit 11403, a communication unit 11404, and a camera head control unit 11405. The CCU 11201 includes a communication unit 11411, an image processing unit 11412, and a control unit 11413. The camera head 11102 and the CCU 11201 are communicably connected to each other by a transmission cable 11400.

The lens unit 11401 is an optical system provided to a portion connecting with the lens barrel 11101. The observation light received from the distal end of the lens barrel 11101 is guided to the camera head 11102 and is incident on the lens unit 11401. The lens unit 11401 is configured by combining a plurality of lenses including zoom lenses and focus lenses.

The imaging element constituting the imaging unit 11402 may be one (so-called single plate type) or a plurality of (so-called multi plate type) imaging elements. In a case where the imaging unit 11402 is configured as a multi-plate type, image signals corresponding to R, G, and B may be generated, for example, by respective imaging elements, and a color image may be obtained by synthesizing the image signals. Alternatively, the imaging unit 11402 may include a pair of imaging elements for acquiring right-eye and left-eye image signals corresponding to 3D display, respectively. By performing the 3D display, the surgical operator 11131 can more accurately grasp the depth of a living tissue in a site of surgical operation. In addition, in a case where the imaging unit 11402 is configured as a multi-plate type, the lens unit 11401 can also be provided in a plurality of systems, corresponding to each imaging element.

In addition, the imaging unit 11402 may not be necessarily provided in the camera head 11102. For example, the imaging unit 11402 may be provided inside the lens barrel 11101 immediately behind the objective lens.

The driving unit 11403 is configured with an actuator and moves the zoom lens and the focus lens of the lens unit 11401 by a predetermined distance along the optical axis under the control of the camera head control unit 11405. As a result, the magnification and focus of the captured image by the imaging unit 11402 can be appropriately adjusted.

The communication unit 11404 is configured with a communication device for transmitting and receiving various types of information to and from the CCU 11201. The communication unit 11404 transmits the image signal obtained from the imaging unit 11402 as a RAW data to the CCU 11201 via the transmission cable 11400.

In addition, the communication unit 11404 receives a control signal for controlling driving of the camera head 11102 from the CCU 11201 and supplies the control signal to the camera head control unit 11405. The control signal includes information associated with imaging conditions of, for example, information indicating designation of a frame rate of a captured image, information indicating designation of an exposure value at the time of imaging, information indicating designation of magnification and focus of a captured image, and/or the like.

In addition, the imaging conditions such as the above-described frame rate, exposure value, magnification, and focus may be appropriately designated by the user or may be automatically set by the control unit 11413 of the CCU 11201 on the basis of the acquired image signal. In the latter case, so-called Auto Exposure (AE) function, Auto Focus (AF) function, and Auto White Balance (AWB) function are installed in the endoscope 11100.

The camera head control unit 11405 controls the driving of the camera head 11102 on the basis of a control signal from the CCU 11201 received via the communication unit 11404.

The communication unit 11411 is configured with a communication device for transmitting and receiving various types of information to and from the camera head 11102. The communication unit 11411 receives an image signal transmitted from the camera head 11102 via the transmission cable 11400.

In addition, the communication unit 11411 transmits the control signal for controlling the driving of the camera head 11102 to the camera head 11102. The image signal and the control signal can be transmitted by electric communication, optical communication, or the like.

The image processing unit 11412 performs various types of image processes on the image signal which is a RAW data transmitted from the camera head 11102.

The control unit 11413 performs various types of control related to imaging by a site of surgical operation or the like by the endoscope 11100 and displaying of captured images obtained by imaging of the site of surgical operation or the like. For example, the control unit 11413 generates the control signal for controlling the driving of the camera head 11102.

In addition, the control unit 11413 causes the display apparatus 11202 to display the captured image reflecting the site of surgical operation or the like on the basis of the image signal subjected to the image process by the image processing unit 11412. In this case, the control unit 11413 may recognize various objects in the captured image by using various image recognition technologies. For example, by detecting the shape of edge, color, and the like of the object included in the captured image, the control unit 11413 can recognize a surgical tool such as a forceps, a specific body portion, bleeding, a mist at the time of using the energy treatment tool 11112, and the like. When causing the display apparatus 11202 to display a captured image, the control unit 11413 may superimposedly display various types of surgery support information on the image of the site of surgical operation by using the recognition result. The surgery support information is superimposedly displayed and presented to the surgical operator 11131, so that it may be possible to reduce the burden on the surgical operator 11131 and to allow the surgical operator 11131 to reliably perform the surgery.

A transmission cable 11400 that connects the camera head 11102 and the CCU 11201 is an electric signal cable compatible with electric signal communication, an optical fiber compatible with optical communication, or a composite cable thereof.

Herein, in the illustrated example, communication is performed by wire using the transmission cable 11400, but communication between the camera head 11102 and the CCU 11201 may be performed wirelessly.

The technology according to the present disclosure can be suitably applied to the control unit 11413 out of the configurations described above.

For example, the control unit 11413 acquires the information associated with the surgical operator and the dominant hand thereof as input information from the image from a surgical field camera (not illustrated) or previously input information. On the basis of the acquired input information, the control unit 11413 sets a behavior detection parameter used for detecting operations in the surgery performed by the surgical operator.

Furthermore, the control unit 11413 analyzes the steps of surgery in the image from the surgical field camera on the basis of the set behavior detection parameter and controls the imaging of the surgical field camera on the basis of the analysis result.

As described above, by applying the technology according to the present disclosure to the control unit 11413, the behavior detection parameters used for detecting operations related to the surgery are set, so that the accuracy of the step analysis of the surgery can be improved.

In addition, the embodiments of the present disclosure are not limited to the above-described embodiments, and various modifications are possible without departing from the spirit of the present disclosure.

In addition, the effects described in this specification are merely examples and are not limited, and other effects may be provided.

Furthermore, the present disclosure may have the following configuration.

(1)

An information processing apparatus including:

processing circuitry configured to:

set a behavior detection parameter corresponding to a behavior of a subject based on input information corresponding to characteristics of a subject in an image, and detect a behavior of the subject based on the set behavior detection parameter and a posture of the subject in the image.

(2)

The information processing apparatus according to (1), wherein the processing circuitry is further configured to set the behavior detection parameter by adjusting a threshold value for each type of behavior of the subject based on the input information.

(3)

The information processing apparatus according to (1)-(2), wherein the characteristics of the subject include at least one of age, gender, or race of the subject.

(4)

The information processing apparatus according to (1)-(3), wherein the input information is information representing a physical characteristic of the subject.

(5)

The information processing apparatus according to (1)-(4), wherein the behavior of the subject is an action the subject takes during a lecture.

(6)

The information processing apparatus according to (5), wherein the action includes at least one of standing, sitting, or raising a hand.

(7)

The information processing apparatus according to (1)-(6), wherein the processing circuitry sets a respective behavior detection parameter for each of a plurality of subjects in the image.

(8)

The information processing apparatus according to (1)-(7), wherein the processing circuitry is further configured to control an imaging apparatus, which captures a further image based on the detected behavior of the subject.

(9)

The information processing apparatus according to (8), wherein the processing circuitry is further configured to control an imaging angle of view of the imaging apparatus based on the detected behavior of the subject.

(10)

The information processing apparatus according to (8)-(9), wherein the processing circuitry is further configured to control a range of image crop based on the detected behavior of the subject.

(11)

The information processing apparatus according to (1)-(10), wherein the processing circuitry is further configured to set the behavior detection parameter based on the input information, which is acquired from the image.

(12)

The information processing apparatus according to (1)-(11), wherein the processing circuitry is further configured to set the behavior detection parameter based on the input information, which is acquired from information previously recorded in a recording apparatus.

(13)

The information processing apparatus according to (1)-(12), wherein the processing circuitry is further configured to set the behavior detection parameter based on the input information, which is acquired from information input via a user interface.

(14)

The information processing apparatus according to (13), wherein the user interface displays information regarding a classroom and the subject in the image.

(15)

The information processing apparatus according to (14), wherein the user interface displays information regarding a plurality of subjects and a position of the plurality of subjects in the classroom.

(16)

The information processing apparatus according to (13), wherein the user interface displays information corresponding to the detected behavior of the subject.

(17)

The information processing apparatus according to (2), wherein the processing circuitry is further configured to adjust the threshold value in response to selection of the threshold value via a user interface.

(18)

The information processing apparatus according to (1)-(17), wherein the input information further includes object detection information corresponding to an object detected in the image, and wherein the processing circuitry is further configured to control display position information indicating a position of the subject in space, where the position of the subject is determined based on the object information.

(19)

The information processing apparatus according to (1)-(17), wherein the behavior detection parameter includes information corresponding to a predicted motion of the subject.

(20)

An information processing method implemented by an information processing apparatus including processing circuitry, including:

setting, by the processing circuitry, a behavior detection parameter based on input information corresponding to characteristics of a subject in an image; and detecting, by the processing circuitry, a behavior of the subject based on the set behavior detection parameter and a posture of the subject in the image.

(21)

A non-transitory computer readable medium having stored thereon a program that when executed by processing circuitry of a computer causes the processing circuitry to implement a method including:

setting, by the processing circuitry, a behavior detection parameter based on input information corresponding to characteristics of a subject in an image; and detecting, by the processing circuitry, a behavior of the subject based on the set behavior detection parameter and a posture of the subject in the image.

REFERENCE SIGNS LIST

10 Imaging apparatus
20 Information processing apparatus
30 Input/output apparatus
40 Recording apparatus 51 Input information acquisition unit
52 Parameter setting unit
53 Behavior detection unit
54 Imaging control unit
71 Posture detection unit
72 Face detection unit
73 Object detection unit
74 Age/gender estimation unit
75 Person identification unit
76 Parameter setting unit
77 Behavior detection unit
78 Imaging control unit
79 Display control unit

The invention claimed is:

1. An information processing apparatus, comprising:
processing circuitry configured to:
 identify an identity of a subject in an image;
 determine whether the identity of the subject is registered in association with a first behavior detection parameter;
 in response to the identity of the subject being determined as registered in association with the first behavior detection parameter, set a determined behavior detection parameter for the subject based on the first behavior detection parameter;
 in response to the identity of the subject being determined as not registered in association with any behavior detection parameter,
  adjust a default behavior detection parameter based on input information corresponding to characteristics of the subject to obtain a second behavior detection parameter, and
  set the determined behavior detection parameter for the subject based on the second behavior detection parameter; and
 detect a behavior of the subject based on the determined behavior detection parameter and a detected posture of the subject in the image.

2. The information processing apparatus according to claim 1, wherein the characteristics of the subject include at least one of age, gender, or race of the subject.

3. The information processing apparatus according to claim 1, wherein the input information is information representing a physical characteristic of the subject.

4. The information processing apparatus according to claim 1, wherein the processing circuitry sets a respective determined behavior detection parameter for each of a plurality of subjects in the image.

5. The information processing apparatus according to claim 1, wherein the processing circuitry is further configured to adjust the default behavior detection parameter based on the input information that is acquired from the image.

6. The information processing apparatus according to claim 1, wherein the processing circuitry is further configured to adjust the default behavior detection parameter based on the input information that is acquired from information previously recorded in a recording apparatus.

7. The information processing apparatus according to claim 1, wherein the processing circuitry is further configured to adjust the second behavior detection parameter in response to a user input via a user interface.

8. The information processing apparatus according to claim 1,
 wherein the input information further includes object detection information corresponding to an object detected in the image, and
 wherein the processing circuitry is further configured to control display position information indicating a position of the subject in space, where the position of the subject is determined based on the object detection information.

9. The information processing apparatus according to claim 1, wherein the determined behavior detection parameter includes information corresponding to a predicted motion of the subject.

10. The information processing apparatus according to claim 1, wherein the processing circuitry is further configured to, in response to the behavior of the subject being detected based on the determined behavior detection parameter,
 determine an update behavior parameter for the detected behavior based on the detected posture of the subject, and
 register the identity of the subject in association with the update behavior detection parameter for the detected behavior.

11. The information processing apparatus according to claim 1, wherein the behavior of the subject is an action the subject takes during a lecture.

12. The information processing apparatus according to claim 11, wherein the action includes at least one of standing, sitting, or raising a hand.

13. The information processing apparatus according to claim 1, wherein the processing circuitry is further configured to control an imaging apparatus, which captures a further image based on the detected behavior of the subject.

14. The information processing apparatus according to claim 13, wherein the processing circuitry is further configured to control an imaging angle of view of the imaging apparatus based on the detected behavior of the subject.

15. The information processing apparatus according to claim 13, wherein the processing circuitry is further configured to control a range of image crop based on the detected behavior of the subject.

16. The information processing apparatus according to claim 1, wherein the processing circuitry is further configured to adjust the default behavior detection parameter based on the input information that is acquired from information input via a user interface.

17. The information processing apparatus according to claim 16, wherein the user interface displays information corresponding to the detected behavior of the subject.

18. The information processing apparatus according to claim 16, wherein the user interface displays information regarding a classroom and the subject in the image.

19. The information processing apparatus according to claim 18, wherein the user interface displays information regarding a plurality of subjects and a position of the plurality of subjects in the classroom.

20. An information processing method implemented by an information processing apparatus including processing circuitry, comprising:
 identifying an identity of a subject in an image;
 determining whether the identity of the subject is registered in association with a first behavior detection parameter;
 in response to the identity of the subject being determined as registered in association with the first behavior detection parameter, setting, by the processing circuitry, a determined behavior detection parameter for the subject based on the first behavior detection parameter;

in response to the identity of the subject being determined as not registered in association with any behavior detection parameter, adjusting, by the processing circuitry, a default behavior detection parameter based on input information corresponding to characteristics of a subject to obtain a second behavior detection parameter, and setting, by the processing circuitry, the determined behavior detection parameter for the subject based on the second behavior detection parameter; and detecting, by the processing circuitry, a behavior of the subject based on the determined behavior detection parameter and a detected posture of the subject in the image.

21. A non-transitory computer readable medium having stored thereon a program that when executed by processing circuitry of a computer causes the processing circuitry to implement a method comprising:

identifying an identity of a subject in an image;

determining, whether the identity of the subject is registered in association with a first behavior detection parameter;

in response to the identity of the subject being determined as registered in association with the first behavior detection parameter, setting a determined behavior detection parameter for the subject based on the first behavior detection parameter;

in response to the identity of the subject being determined as not registered in association with any behavior detection parameter, adjusting a default behavior detection parameter based on input information corresponding to characteristics of a subject to obtain a second behavior detection parameter, and setting the determined behavior detection parameter for the subject based on the second behavior detection parameter; and detecting a behavior of the subject based on the determined behavior detection parameter and a detected posture of the subject in the image.

* * * * *